United States Patent
Haran

(10) Patent No.: US 8,821,802 B2
(45) Date of Patent: Sep. 2, 2014

(54) METHOD AND APPARATUS FOR COMPUTER CONTROLLED SCENT DELIVERY

(75) Inventor: Yossi Haran, Modiin (IL)

(73) Assignee: Scentcom Ltd., Lehavot Haviva (IL)

( * ) Notice: Subject to any disclaimer, the term of this patent is extended or adjusted under 35 U.S.C. 154(b) by 346 days.

(21) Appl. No.: 13/143,197

(22) PCT Filed: Jan. 7, 2010

(86) PCT No.: PCT/IL2010/000017
§ 371 (c)(1),
(2), (4) Date: Jul. 4, 2011

(87) PCT Pub. No.: WO2010/079486
PCT Pub. Date: Jul. 15, 2010

(65) Prior Publication Data
US 2011/0268605 A1 Nov. 3, 2011

Related U.S. Application Data

(60) Provisional application No. 61/143,283, filed on Jan. 8, 2009.

(51) Int. Cl.
| | |
|---|---|
| *A62B 7/08* | (2006.01) |
| *A61L 9/12* | (2006.01) |
| *B05B 17/00* | (2006.01) |
| *B05B 17/06* | (2006.01) |
| *A61L 9/14* | (2006.01) |
| *A61L 9/00* | (2006.01) |
| *B05B 15/02* | (2006.01) |
| *A61L 9/03* | (2006.01) |

(52) U.S. Cl.
CPC ........... *A61L 9/122* (2013.01); *A61L 2209/132* (2013.01); *B05B 17/0646* (2013.01); *B05B 15/02* (2013.01); *B05B 17/0669* (2013.01); *A61L 2209/11* (2013.01); *A61L 9/125* (2013.01); *A61L 9/03* (2013.01); *A61L 9/14* (2013.01)

USPC ........... 422/124; 422/120; 422/123; 422/125; 422/5

(58) Field of Classification Search
CPC ............ A61L 9/03; A61L 9/032; A61L 9/035
USPC .......................... 422/120, 123, 124, 125, 4, 5
See application file for complete search history.

(56) References Cited

U.S. PATENT DOCUMENTS

| | | | |
|---|---|---|---|
| 4,059,422 A | * | 11/1977 | Steiner ........................... 96/147 |
| 4,695,434 A | | 9/1987 | Spector |

(Continued)

FOREIGN PATENT DOCUMENTS

| | | |
|---|---|---|
| EP | 1329228 A1 | 7/2003 |
| EP | 1543844 A2 | 6/2005 |

(Continued)

OTHER PUBLICATIONS

International Search Report for parallel PCT application PCT/IL2010/00017, by European Patent Office of mailing date May 3, 2010.

(Continued)

*Primary Examiner* — Regina M Yoo
(74) *Attorney, Agent, or Firm* — Simon Kahn

(57) ABSTRACT

An apparatus for producing a scent, constituted of: a directional air mover arranged to produce an air flow exhibiting an angular velocity in relation to a central linear axis of the air flow; a plurality of electronically controlled scent producing elements arranged about the produced air flow, each of the plurality of electronically controlled scent producing elements distal of the directional air mover such that scent from any of the plurality of electronically controlled scent producing elements are not deposited on any surface of the directional air mover; and a control unit in communication with each of the directional air mover and the plurality of electronically controlled scent producing elements. Preferably, the plurality of electronically controlled scent producing elements is arranged radially about the central linear axis of the air flow.

9 Claims, 20 Drawing Sheets

(56) References Cited

U.S. PATENT DOCUMENTS

| | | |
|---|---|---|
| 4,850,534 A | 7/1989 | Takahashi et al. |
| 5,435,282 A | 7/1995 | Haber et al. |
| 5,972,290 A | 10/1999 | De Sousa |
| 6,024,783 A | 2/2000 | Budman |
| 6,136,277 A | 10/2000 | Nardini |
| 6,149,873 A | 11/2000 | Potter et al. |
| 6,152,829 A | 11/2000 | Jaidka |
| 6,325,475 B1 | 12/2001 | Hayes et al. |
| 6,530,370 B1 | 3/2003 | Heinonen |
| 6,536,746 B2 | 3/2003 | Watkins |
| 6,539,937 B1 | 4/2003 | Haveri |
| 6,581,915 B2 | 6/2003 | Bartsch et al. |
| 6,592,104 B2 | 7/2003 | Cox |
| 6,602,475 B1 | 8/2003 | Chiao |
| 6,656,041 B1 | 12/2003 | Kaminkow |
| 6,800,119 B2 * | 10/2004 | Huang .................. 96/226 |
| 6,962,151 B1 | 11/2005 | Knoch et al. |
| 7,040,548 B2 | 5/2006 | Rodgers |
| 7,160,515 B2 | 1/2007 | Murdell et al. |
| 7,223,361 B2 | 5/2007 | Kvietok et al. |
| 7,437,061 B2 | 10/2008 | Manne |
| 2003/0107139 A1 | 6/2003 | Wohrle |
| 2004/0164101 A1 | 8/2004 | Cornet et al. |
| 2006/0289673 A1 | 12/2006 | Wang et al. |
| 2007/0189919 A1 | 8/2007 | Prince et al. |
| 2007/0280653 A1 * | 12/2007 | Viera .................. 392/395 |
| 2008/0043204 A1 | 2/2008 | Guo |
| 2008/0135640 A1 * | 6/2008 | Velazquez et al. .......... 239/24 |
| 2008/0191370 A1 | 8/2008 | Pankhurst et al. |

FOREIGN PATENT DOCUMENTS

| | | |
|---|---|---|
| WO | 0012143 | 3/2000 |
| WO | 0232470 A1 | 4/2002 |
| WO | 03028775 A1 | 4/2003 |
| WO | 03059403 A1 | 7/2003 |
| WO | 2004105878 A1 | 12/2004 |
| WO | 2005092400 A1 | 10/2005 |
| WO | 2006058125 A2 | 6/2006 |
| WO | 2006074562 A1 | 7/2006 |

OTHER PUBLICATIONS

Written Opinion of the International Searching Authority regarding the International Search Report for parallel PCT application PCT/IL2010/00017, by European Patent Office of mailing date May 3, 2010.

Office action dated Apr. 2, 2013 by Israel Patent Office for Parallel Application IL213910.

* cited by examiner

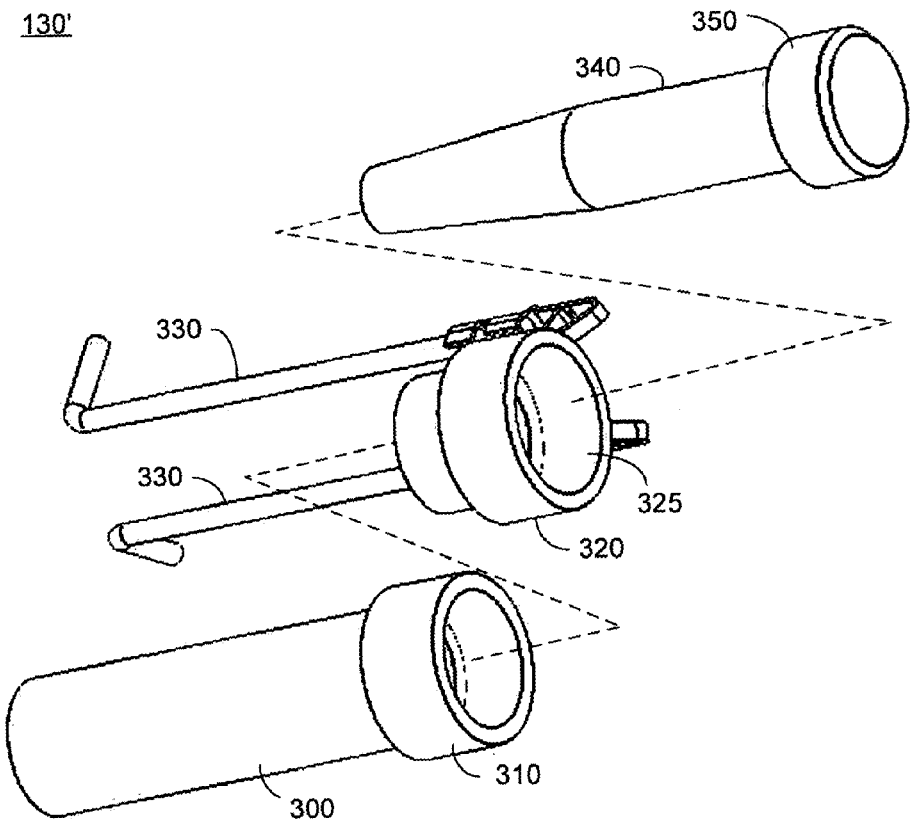
FIG. 4A
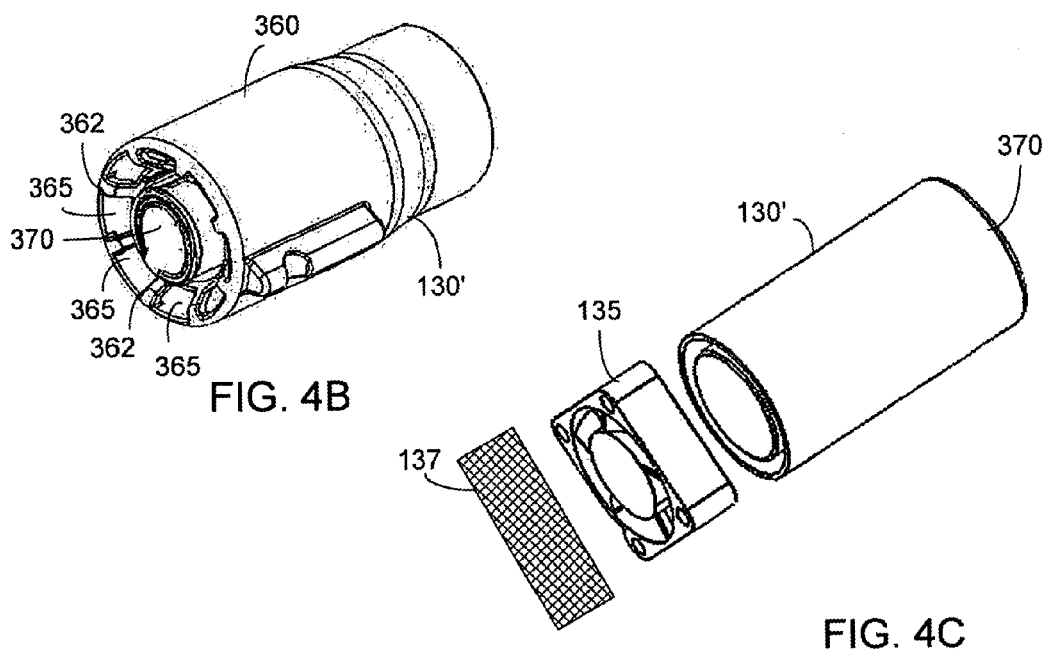
FIG. 4B
FIG. 4C

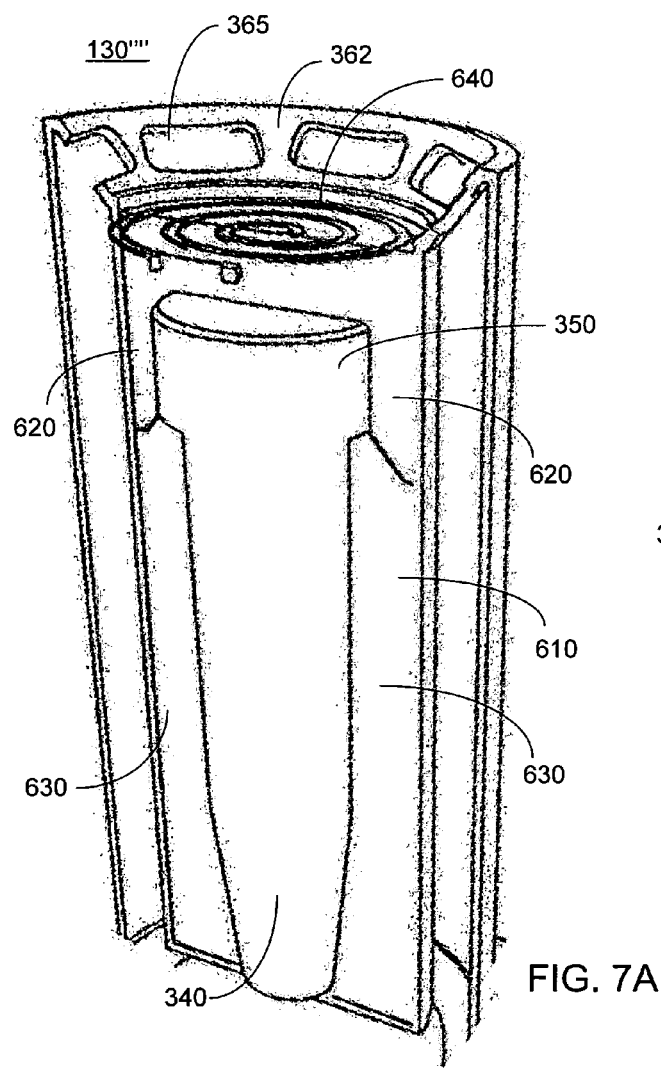
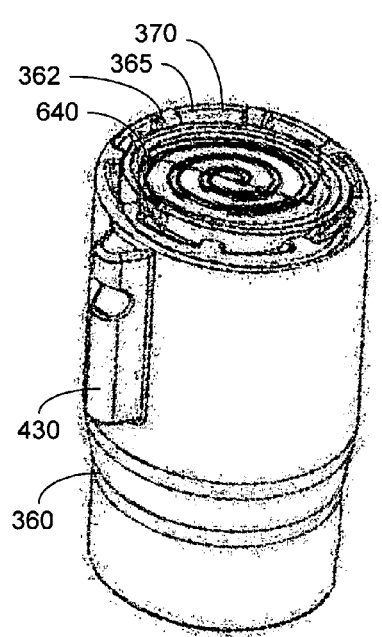
FIG. 7A
FIG. 7B

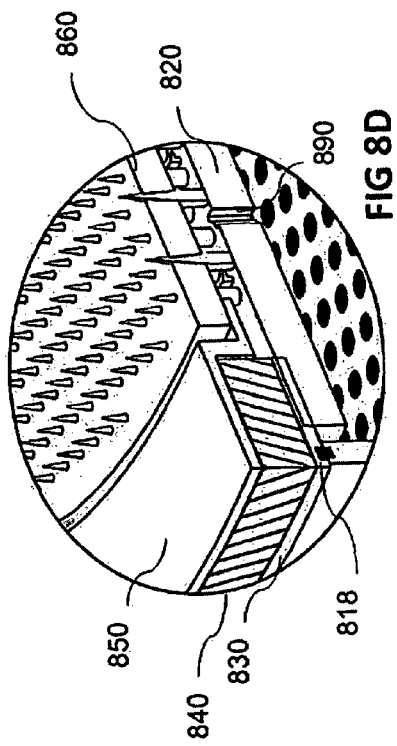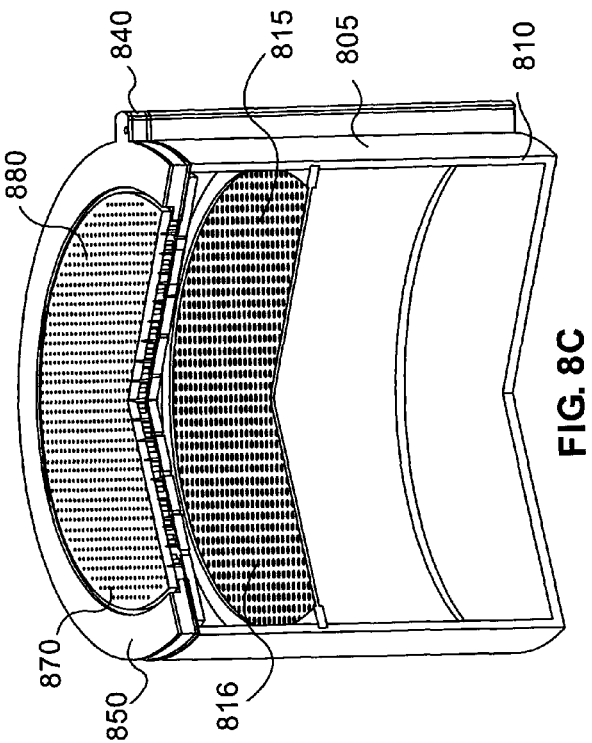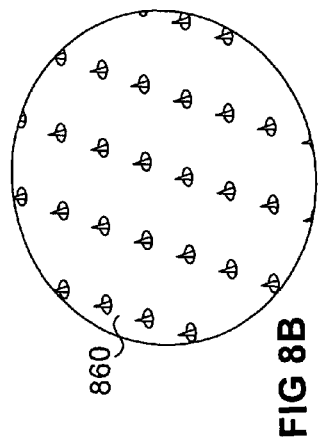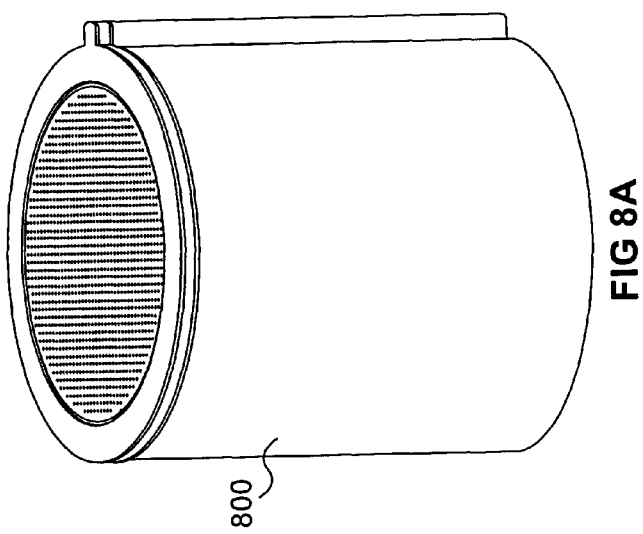

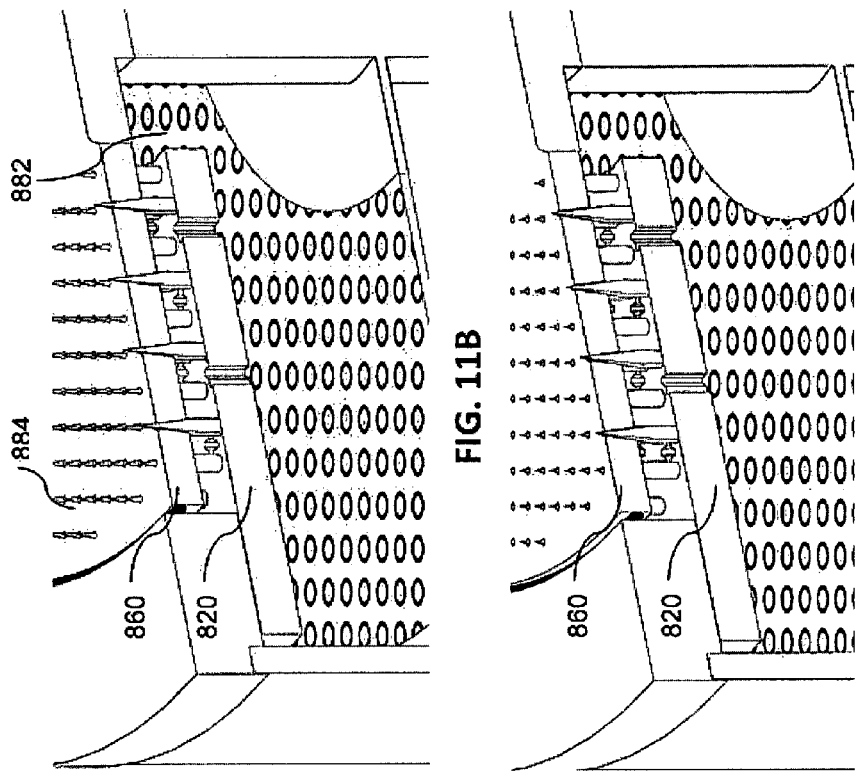
FIG. 11B
FIG. 11C
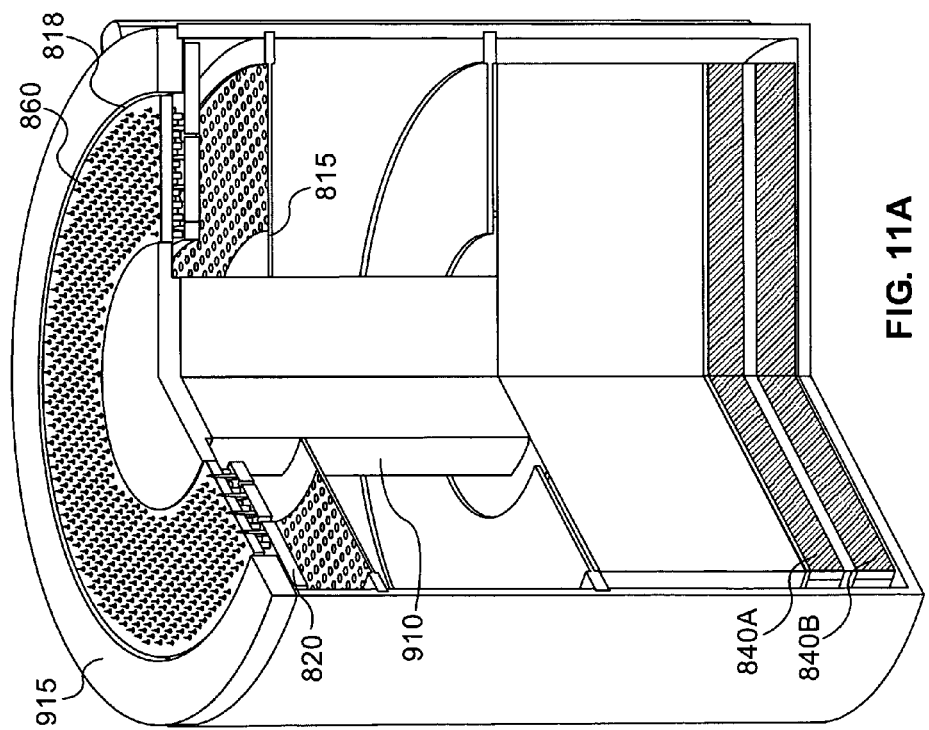
FIG. 11A

METHOD AND APPARATUS FOR COMPUTER CONTROLLED SCENT DELIVERY

CROSS-REFERENCE TO RELATED APPLICATIONS

This application claims priority to U.S. Provisional Patent Application Ser. No. 61/143,283 filed Jan. 8, 2009, entitled "Method and Apparatus for Computer Controlled Scent Delivery", the entire contents of which are incorporated herein by reference.

TECHNICAL FIELD

The invention relates generally to the field of electronically controlled scent production, and more particularly to an apparatus with a plurality of electronically controlled nebulizers disposed radially about a central air stream producer.

BACKGROUND

Video games, particularly computer based games and game stations, have become extremely popular. The combination of visual and audio stimulation has succeeded in capturing a significant portion of people's leisure time. Various games have been developed, with associated hardware, that further involve the sense of touch, by allowing for varying input instruments. In one example, a musical instrument such as a mock guitar, is utilized as a game input, thus involving the sense of touch.

Games have been developed providing for a virtual reality world, again based on stimulating various user senses. However, to date, the remaining senses, namely smell and taste have not been stimulated.

U.S. Pat. No. 6,656,041 issued Dec. 2, 2003 to Kaminkow et al, the entire contents of which is incorporated herein by reference, provides for a method and apparatus for emulating a storm as part of a gaming device, preferably as a topper unit including a blower to create an air stream, an illumination source to emulate lightning, and a sound card arranged to transmit thunder. Thus, the sense of touch is stimulated, in addition to the sense of hearing and seeing.

U.S. Patent Application Publication S/N 2008/0043204 published Feb. 21, 2008 to Guo, is addressed to a digital scent movie projector with sound channels. Scent making devices release a scent into a cinema, thereby providing for film arts to provide a sense of sight, hearing and smell as part of movie.

A movie proceeds along a predetermined script, which does not allow for user interaction. Thus, the scent to be provided by Guo, are predetermined, and are not subject to change by a user action. Additionally, scent provided by Guo is arranged for releasing scent into a large space, which is not appropriate for an individual playing a computer game.

An additional problem with many prior art solutions is residual scent; particularly the scent continues to linger for a relatively long period after the desired emission. Residual scent is particularly problematic in the case of individual computer garners, which often play in undisturbed spaces, where scents easily linger. In particular, any physical element which has been contacted by a concentration of scent molecules continues to exude the scent. The residual scent further contaminates additional scents, which may need to be rapidly emitted in line with progress of the game.

World Intellectual Property Organization publication WO 02/32470 A1 published 25 Apr. 2002 to SENEIT, Inc. is addressed to an apparatus for emitting an odor. Unfortunately, the apparatus as described suffers greatly from the aforementioned residual scent, as scent molecules are deposited along the enclosed spaces of scented air travel.

Various nebulizer schemes are known to the prior art, including placing a vibrating fine mesh in contact with a liquid to be nebulized. The mesh typically is arranged to be sufficiently fine so as to block any flow of the liquid and is vibrated, typically at ultrasonic frequencies, thereby atomizing the liquid. Unfortunately, such a scheme suffers from certain drawbacks, such as spontaneous scent leakage since there is no means to prevent spontaneous release of volatile vapors via the mesh opening. Furthermore any molecules adhering to the mesh walls may be released without further vibration, further leading to residual scents. Additionally, there is a tendency for the fine mesh to become blocked by the aromatic molecules adhering to the mesh openings. Furthermore, the mesh aperture which is fixed in size is designed for a particular molecule size and viscosity, and a particular fixed mesh based nebulizer can not be used for a plurality of liquids having a range of viscosity without changing the fixed mesh.

U.S. Patent Application Publication S/N 2007/0189919 published Aug. 17, 2007 to Prince et al, the entire contents of which is incorporated herein by reference, is addressed to a method for cleaning a medicament from a portion of a nebulizer. In particular, the above mentioned application is addressed to the problem of prior art mesh based nebulizers becoming occluded.

Thus, there is a need for an electronically controlled nebulizer addressing the issue of residual scent and arranged to avoid occlusion.

SUMMARY

Accordingly, it is a principal object of the present invention to overcome at least some of the disadvantages of prior art. This is accomplished in certain embodiments by providing a plurality of electronically controlled scent emitters arrayed about a central air mover, such as a fan. The central air mover drives an air flow towards a target user, and draws the scent emitted from the electronically controlled scent emitters, preferably by creating a reduced pressure zone near the electronically controlled scent emitters. In one embodiment, the central air mover is operative at a plurality of air flow rates, and is preferably operative to perform air circulation within the area of the user. Preferably the central air mover is arranged to provide air rotation thus imparting an angular velocity to the air flow, creating a vortex. The resultant vortex mixes the scents drawn from the electronically controlled scent emitters.

In one embodiment, each of the electronically controlled scent emitters further comprises an associated individual air mover, preferably a fan mounted distally of the electronically controlled scent emitters in relation to the target user. The individual air mover is preferably reversible, and thus may be operated to generate a forward air stream generally directed towards the target user or a reverse air stream generally withdrawing the scent output by the electronically controlled scent emitter from the target user. In one particular embodiment, a scent disposer is further provided arranged to dispose of the scent carried by reverse generated air stream.

In certain embodiments, each of the central air mover, the plurality of electronically controlled scent emitters and the optional individual air movers are responsive to commands from a control unit. The control unit is preferably in communication with a processor of a computer interfacing with the target user, and operative responsive thereto to generate a desired scent to be experienced by the target user. The experienced scent is in one embodiment output by a single one of the electronically controlled scent emitters, and in another embodiment output by a combination of the outputs of more than one of the electronically controlled scent emitters.

In one embodiment, each of the electronically controlled scent emitters is constituted of a porous material impregnated with a volatile scent based fluid in communication with a heat element, the porous material emitting a scent responsive to the heat element elevating the volatile scent based fluid to at least a predetermined temperature. In one particular embodiment, the heat element is a ring shaped element surrounding the sponge like material. In another embodiment, the heat element is in contact with an intermediate gas permeable element, substantially unaffected by heat, such as a stone or clay based material. The intermediate gas permeable element preferably contactingly surrounds the porous material, and transfers heat thereto while passing the exuded scent.

In one embodiment each of the electronically controlled scent producing elements comprises: a plate exhibiting a plurality of perforations extending from a first face of the plate to a second face of the plate opposing the first face; a volatile scent liquid in physical contact with the first face of the plate; a plurality of plugs juxtaposed with the plate, each of the plugs extending longitudinally from a base end to a tip end, and arranged to mate with one of the plurality of perforations; a translation mechanism in communication with one of the plate and the plurality of plugs, the translation mechanism arranged to translate the set of plugs in relation to the plate from a first position wherein each of the plugs is seated flush within a respective one of the perforations to a second position wherein each of the plugs is at least partially removed from a wall of the respective one of the perforations; and a vibrator in communication with at least one of the plate and the plurality of plugs. Preferably, each of the plugs exhibits a generally conically shaped taper towards the tip end and wherein each of the perforation are generally conically shaped, the base of the generally conically shaped perforations facing the base end of the plugs.

In one embodiment, the computer interfacing with the target user further provides a prediction module, operative to predict a required scent to be delivered to the user in advance of the actual event requiring scent delivery to the target user. The prediction module is further operative in cooperation with the control unit to begin production of the predicted scent by energizing one or more electronically controlled scent emitters. In the event that the processor determines that the event requiring scent delivery to the target user of the predicted scent occurs within a predetermined time window, the optional individual air mover associated with the energized one or more electronically controlled scent emitters are activated to generate a forward air stream generally directed towards the target user. The central air mover is preferably further operated at an increased air flow rate so as to drive the desired scent towards the target user.

In the event that the processor determines that the event requiring scent delivery to the target user of the predicted scent does not occur within the predetermined time window, i.e. that a false prediction has occurred, the energized one or more electronically controlled scent emitters are de-energized and preferably, the optional individual air mover associated with the now de-energized one or more electronically controlled scent emitters are activated to generate a reverse air stream generally directed away from the target user. Preferably the reverse air stream is directed towards the optional scent disposer. The central air mover is preferably further operated at a minimal air flow rate, or de-energized, so as to prevent the flow of the improperly predicted scent from arriving at the target user.

Independently, the invention provides for a method of electronically controlled scent production, comprising: producing an air flow exhibiting an angular velocity in relation to a central linear axis of the air flow; and providing a plurality of electronically controlled scent producing elements; arranging the provided plurality of electronically controlled scent producing elements about the produced turbulent air flow, such that each of the provided plurality of electronically controlled scent producing elements is distal of the source of the produced air flow such that scent from any of the plurality of electronically controlled scent producing elements are not deposited on any surface of the source of air flow.

In one embodiment the method further comprises: arranging the plurality of electronically controlled scent producing elements equidistantly from a central linear axis of the produced air flow. In another embodiment the method further comprises: directing the produced air flow to produce a reduced pressure zone at the output of each of the provided plurality of electronically controlled scent producing elements, thereby drawing the scent output from each of the electronically controlled scent producing elements into the produced air flow. In one yet further embodiment, the method comprises: increasing the velocity of air flow in relation to an initial source thereby producing the reduced pressure zone.

In one embodiment the produced air flow is at a selectable one of a plurality of air flow rates. In another embodiment the method further comprises for each of the provided electronically controlled scent producing elements in the event that the selectable electronically controlled scent producing element is to produce scent: moving air associated with the selectable one of the provided electronically controlled scent producing elements in a first direction to drive the scent output of the selectable electronically controlled scent producing element towards the air flow. In one yet further embodiment, the method further comprises for each of the provided electronically controlled scent producing elements in the event that the selectable electronically controlled scent producing element is to cease scent production: moving air associated with the selectable one of the provided electronically controlled scent producing elements in a second direction opposing the first direction to withdraw the scent output of the respective electronically controlled scent producing element from the air flow. In yet another further embodiment the method further comprises disposing of the withdrawn scent output. Preferably, the disposing is accomplished by a charcoal element.

In one embodiment the method further comprises: operating more than one of the electronically controlled scent producing elements simultaneously to produce a single combined scent. In another embodiment wherein each of the provided electronically controlled scent producing elements comprises a scent impregnated absorbent material, the method further comprises: heating the scent impregnated absorbent material to a predetermined temperature so as to produce a particular scent.

In another embodiment wherein each of the provided electronically controlled scent producing elements further comprises an intermediate gas permeable element, the scent impregnated absorbent material at least partially contactingly surrounded by the intermediate gas permeable element, wherein the heating is through the intermediate gas permeable element.

In yet another embodiment, wherein each of the provided electronically controlled scent producing elements comprises: a plate exhibiting a plurality of perforations extending from a first face of the plate to a second face of the plate opposing the first face; a volatile scent liquid in physical contact with the first face of the provided plate; and a plurality of plugs juxtaposed with the plate, each of the plugs extending longitudinally from a base end to a tip end, and arranged to mate with one of the plurality of perforations, the method further comprising: translating the set of plugs in relation to the plate from a first position wherein each of the plugs is seated flush within a respective one of the perforations to a second position wherein each of the plugs is at least partially removed from a wall of the respective one of the perforations; and vibrating at least one of the provide plate and the plurality of plugs with ultrasonic energy to thereby produce a scent.

Additional features and advantages of the invention will become apparent from the following drawings and description.

BRIEF DESCRIPTION OF THE DRAWINGS

For a better understanding of various embodiments of the invention and to show how the same may be carried into effect, reference will now be made, purely by way of example, to the accompanying drawings in which like numerals designate corresponding elements or sections throughout.

With specific reference now to the drawings in detail, it is stressed that the particulars shown are by way of example and for purposes of illustrative discussion of the preferred embodiments of the present invention only, and are presented in the cause of providing what is believed to be the most useful and readily understood description of the principles and conceptual aspects of the invention. In this regard, no attempt is made to show structural details of the invention in more detail than is necessary for a fundamental understanding of the invention, the description taken with the drawings making apparent to those skilled in the art how the several forms of the invention may be embodied in practice. In the accompanying drawings:

FIGS. 4A-4C illustrate various views of a first exemplary embodiment of an electronically controlled scent producing element comprising a heating element in cooperation with a scent impregnated absorbent material, the views being described taken together, in accordance with an exemplary embodiment;

FIGS. 7A-7B illustrate various views of a fourth exemplary embodiment of an electronically controlled scent producing element comprising a heating element in cooperation with a scent impregnated absorbent material, the views being described taken together;

FIGS. 8A-8J illustrate various views of an exemplary embodiment of an electronically controlled scent producing element comprising a plurality of micro-plugs and a perforated plate juxtaposed with the plurality of micro-plugs, in accordance with an exemplary embodiment;

FIGS. 11A-11C illustrate a third alternative embodiment for the scent producing element of FIG. 8A, in which a separate translation mechanism and vibrator are supplied, the vibrator arranged to vibrate only the perforated plate, in accordance with an exemplary embodiment;

DETAILED DESCRIPTION

Figure 1:
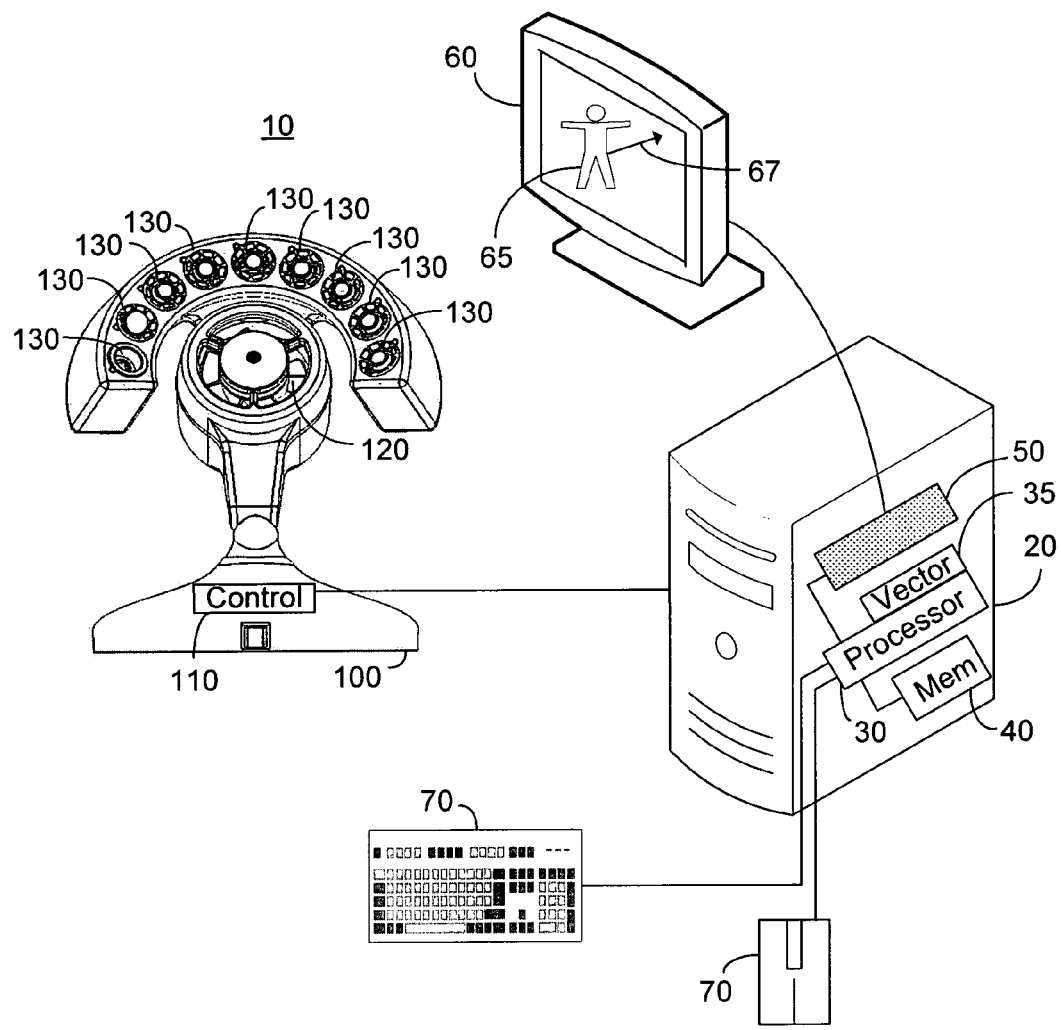
FIG. 1 illustrates a high level block diagram of a system for computer interaction including scent production.

Before explaining at least one embodiment in detail, it is to be understood that the invention is not limited in its application to the details of construction and the arrangement of the components set forth in the following description or illustrated in the drawings. The invention is applicable to other embodiments or of being practiced or carried out in various ways. Also, it is to be understood that the phraseology and terminology employed herein is for the purpose of description and should not be regarded as limiting.

FIG. 1 illustrates a high level block diagram of a system 10 for computer interaction including scent production, the system comprising: a computing platform 20 comprising a processor 30, a vector determining functionality 35, a memory 40 and a graphics card 50; a display device 60 displaying a user controlled character 65 exhibiting a vector of travel 67; one or more user input devices 70 illustrated without limitation as a keyboard and a pointing device; and a scent producer 100 comprising a control unit 110, a directional air mover 120 and a plurality of electronically controlled scent producing elements 130. Processor 30 is in communication with each of memory 40, graphics card 50, one or more user input devices 70 and scent producer 100, particularly control unit 110. Vector determining functionality 35 is constituted a portion of a run time engine loaded within processor 30, however this is not meant to be limiting in any way. Vector determining functionality 35 may be further associated with graphics card 50, without exceeding the scope. There is no requirement that the communication links with processor 30 all be of the same type. In one non-limiting embodiment, the communication link between processor 30 and scent producer 100 is via a universal serial bus. Control unit 110 is in communication with each of electronically controlled scent producing elements 130.

In operation, and as will be described further below, computing platform 20 runs a set of computer readable instructions stored on memory 40 resulting in a particular display on display device 60, including user controlled character 65, preferably via graphics card 50. In one non-limiting example, the set of computer readable instructions comprises a video computer game. The user controlled character is manipulated by a user utilizing user input devices 70. Additionally, computing platform 20 runs a set of computer readable instructions operative to perform the method described below, particularly in relation to FIG. 2. In one non-limiting embodiment, the method is implemented as a run time engine loaded separately from the video computer game.

Responsive to predetermined events, processor 30 further commands scent producer 100, and in particular control unit 110 to produce a particular scent from one or more of electronically controlled scent producing elements 130. Scent production typically requires a minimal time period, and thus the computer readable instructions on memory 40 further preferably comprise a prediction model arranged to monitor user controlled character 65, determine a vector of travel of the user controlled character by vector determining functionality 35, and in the event that vector 67 of user controlled character 65 enters within a predetermined first radius of a scent event, processor 30 is operative to begin scent production by scent producer 100 in accordance with the scent event. The term vector as used herein is meant to include both position, direction of travel and rate of travel, with the vector length reflecting the rate of travel, and is typically not shown on display 60. In one embodiment, scent production may comprise a mix of a plurality of produced scents, i.e. a scent from a plurality of electronically controlled scent producing elements 130, or a selectable one of electronically controlled scent producing elements 130.

Preferably, in the event that within a predetermined time frame vector 67 of user controlled character 65 has not entered within a second smaller radius of the scent event, or vector 67 has left the first radius, scent production from electronically controlled scent producing elements 130 is stopped, and preferably any produced scent is disposed of In the event that within the predetermined time vector 67 of user controlled character 65 has entered within the second smaller radius of the scent event, in one embodiment directional air mover 120 is energized to a greater rate so as to drive the scent produced by electronically controlled scent producing elements 130 towards the user. In another embodiment, the actual position of character 65 is used in relation to the first radius, and vector 67 is used in relation to the second radius.

In one embodiment, to be described further hereinto below, disposal of any produced scent is accomplished in cooperation with an individual electronically controlled air mover associated with each of the plurality of electronically controlled scent producing elements 130, in particular by operating the individual electronically controlled air mover to withdraw the scent from a centrally produced air flow. Further preferably, the withdrawn scent is driven into a charcoal packet which absorbs the withdrawn scent.

Figure 2A:
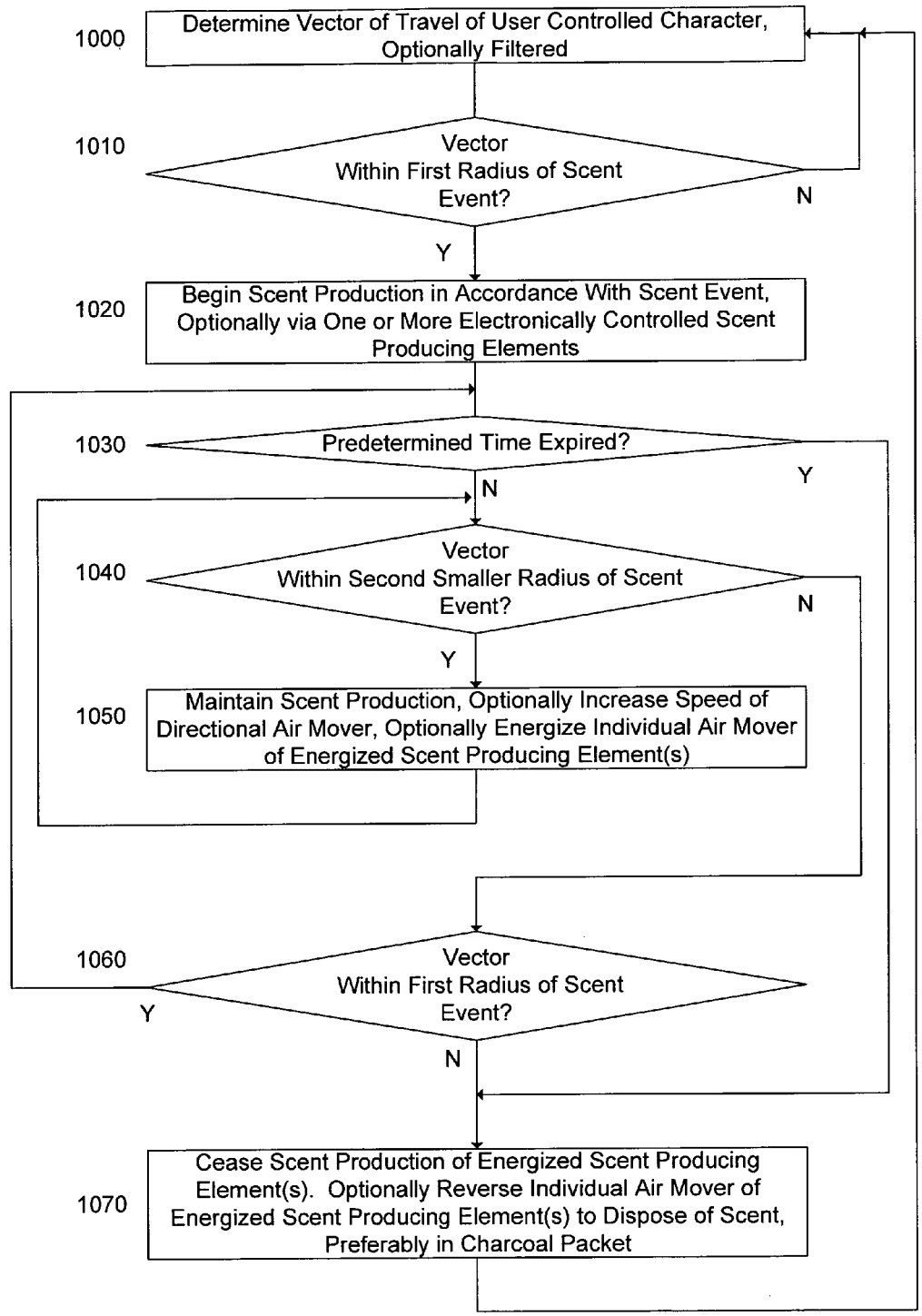
FIG. 2A illustrates a high level flow chart of a computer implemented method of scent production for use with the system of FIG. 1 responsive to vector determination of a user controlled character.

FIG. 2A illustrates a high level flow chart of a first computer implemented method of scent production, preferably stored in memory 40 for operation by processor 30. In stage 1000 vector 67 of travel of user controlled character 65 is determined, preferably by vector determining functionality 35. The term vector as used herein is meant to include both position, direction of travel and rate of travel, with the vector length reflecting the rate of travel. Optionally, vector 67 is a filtered vector, such as by a Kalman filter, to reduce noise.

In stage 1010, vector 67 of user controlled character 65 of stage 1000 is compared with a first event radius of each scent event. In the event that a filter is used, the filtered vector is compared with the first event radius. The term scent event as used herein is meant to include any event or occurrence within the programming of processor 30 for which a preprogrammed scent is designated. In one non-limiting embodiment, processor 30 runs a video game stored on memory 40, and particular scenes within the video game are associated with each one of a plurality of scents. In the event that vector 67 of controlled character 65 is not within the first event radius, stage 1000 described above is again performed.

In the event that in stage 1010 vector 67 of user controlled character 65 is within the first event radius, in stage 1020 scent production in accordance with the scent event is begun. In one embodiment, scent production is performed by energizing one more of electronically controlled scent producing elements 130 of scent producer 100, by transmitting appropriate commands to control unit 110. The size of the first event radius is selected to take into account the delayed response of scent producer 100, which requires a substantial amount of time to produce a scent, typically on the order of 1-2 seconds. Thus, stages 1010 and 1020 perform scent prediction, to predict the requirement for a scent in advance of the actual need thereof.

In stage 1030, the elapsed time from the beginning of operation of stage 1020 is compared with a predetermined time, the predetermined time being associated with the time required for scent production. In one non-limiting embodiment, different predetermined times are stored associated with different scents, and in another non-limiting embodiment a single time is stored as a predetermined time required for scent production, the single time selected to be at least long enough for each of the plurality of electronically controlled scent producing elements 130 to being scent production.

In the event that the predetermined time has not expired, in stage 1040, vector 67 of user controlled character 65 of stage 1000 is compared with a second event radius of the scent event of stage 1010, the second scent radius being smaller than the first radius. In the event that vector 67 of user controlled character 65 is within the second scent radius, i.e. the scent event is active, in stage 1050, scent production of stage 1010 is maintained. Optionally, the speed of air flow produced by directional air mover 120 is increased. Optionally, any individual air movers associated with the energized scent producing elements 130 of stage 1020 are energized to output the produced scent. Stage 1040 described above is again performed. The operation of directional air mover 120 and the individual air movers will be further described hereinto below.

In the event that in stage 1040 vector 67 of user controlled character 65 is not within the second scent radius, in stage 1060 the vector of user controlled character 65 of stage 1000 is compared with the first event radius of the scent event of stage 1010. In the event that the vector of user controlled character 65 is still within the first event radius of the scent event of stage 1010, stage 1030 described above is again performed.

In the event that in stage 1060 vector 67 of user controlled character 65 is not within the first event radius of the scent event of stage 1010, i.e. user controlled character 65 has moved elsewhere, and the predicted scent production of stage 1020 is in error, also known as a false prediction, in stage 1070 scent production of stage 1020 is ceased. In one embodiment, scent production is ceased by de-energizing the one more electronically controlled scent producing elements 130 of scent producer 100 energized in stage 1020, by transmitting appropriate commands to control unit 110. Optionally, any individual air movers associated with the energized scent producing elements 130 of stage 1020 are reverse energized to withdraw any scent produced by the false production from reaching the user. In one optional embodiment the withdrawn scent is disposed of by directing the reverse air flow to a charcoal packet, as will be described further hereinto below. Stage 1000, as described above, is then performed. In the event that in stage 1030 the predetermined time has expired, stage 1070, as described above, is performed.

Figure 2B:
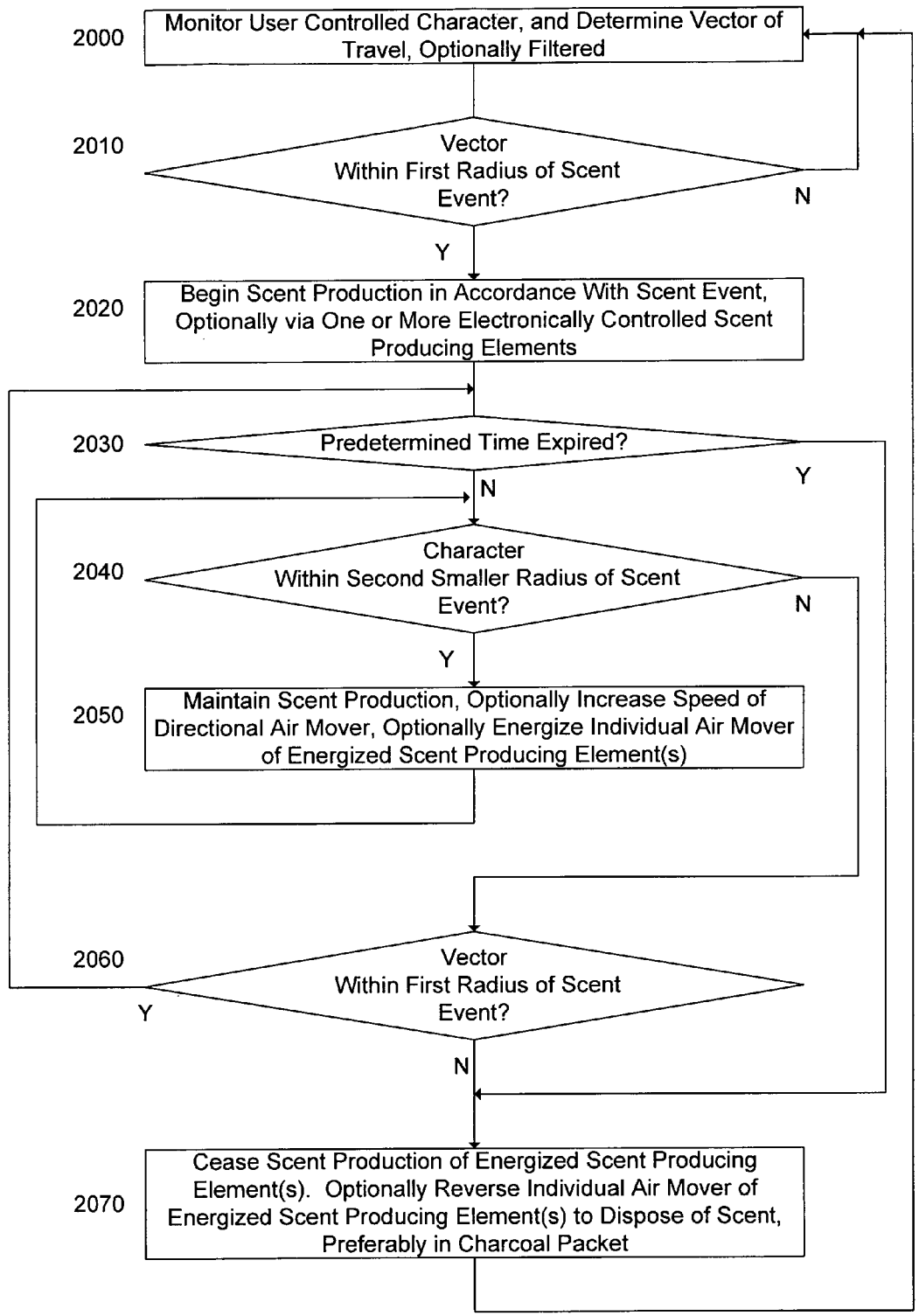
FIG. 2B illustrates a high level flow chart of a computer implemented method of scent production for use with the system of FIG. 1 responsive to vector and position determination of a user controlled character.

FIG. 2B illustrates a high level block diagram of a second computer implemented method of scent production, preferably stored in memory 40 for operation by processor 30. In stage 2000 user controlled character 65 is monitored, and vector 67 of travel is determined, preferably by vector determining functionality 35. The term vector as used herein is meant to include both position, direction of travel and rate of travel, with the vector length reflecting the rate of travel. Optionally, vector 67 is a filtered vector, such as by a Kalman filter, to reduce noise.

In stage 2010, vector 67 of user controlled character 65 of stage 2000 is compared with a first event radius of each scent event. In the event that a filter is used, the filtered vector is compared with the first event radius. The term scent event as used herein is meant to include any event or occurrence within the programming of processor 30 for which a preprogrammed scent is designated. In one non-limiting embodiment, processor 30 runs a video game stored on memory 40, and particular scenes within the video game are associated with each one of a plurality of scents. In the event that vector 67 of controlled character 65 is not within the first event radius, stage 2000 described above is again performed.

In the event that in stage 2010 vector 67 of user controlled character 65 is within the first event radius, in stage 2020, scent production in accordance with the scent event is begun. In one embodiment, scent production is performed by energizing one or more of electronically controlled scent producing elements 130 of scent producer 100, by transmitting appropriate commands to control unit 110. The size of the first event radius is selected to take into account the delayed response of scent producer 100, which requires a substantial amount of time to produce a scent, typically on the order of 1-2 seconds. Thus, stages 2010 and 2020 perform scent prediction, to predict the requirement for a scent in advance of the actual need thereof.

In stage 2030, the elapsed time from the beginning of operation of stage 2020 is compared with a predetermined time, the predetermined time being associated with the time required for scent production. In one non-limiting embodiment, different predetermined times are stored associated with different scents, and in another non-limiting embodiment a single time is stored as a predetermined time required for scent production, the single time selected to be at least long enough for each of the plurality of electronically controlled scent producing elements 130 to being scent production.

In the event that the predetermined time has not expired, in stage 2040, the position of user controlled character 65 of stage 2000 is compared with a second event radius of the scent event of stage 2010, the second scent radius being smaller than the first radius. If the position of user controlled character 65 is within the second scent radius, i.e. the scent event is active, in stage 2050, scent production of stage 2010 is maintained. Optionally, the speed of air flow produced by directional air mover 120 is increased. Optionally, any individual air movers associated with the energized scent producing elements 130 of stage 1020 are energized to output the produced scent. Stage 2040 described above is again performed. The operation of directional air mover 120 and the individual air movers will be further described hereinto below.

In the event that in stage 2040 the position of user controlled character 65 is not within the second scent radius, in stage 2060 the vector of user controlled character 65 of stage 2000 is compared with the first event radius of the scent event of stage 2010. In the event that the vector of user controlled character 65 is still within the first event radius of the scent event of stage 2010, stage 2030 described above is again performed.

In the event that in stage 2060 the position of user controlled character 65 is not within the first event radius of the scent event of stage 2010, i.e. user controlled character 65 has moved elsewhere, and the predicted scent production of stage 2020 is in error, also known as a false prediction, in stage 2070, scent production of stage 2020 is ceased. In one embodiment, scent production is ceased by de-energizing the one more electronically controlled scent producing elements 130 of scent producer 100 energized in stage 2020, by transmitting appropriate commands to control unit 110. Optionally, any individual air movers associated with the energized scent producing elements 130 of stage 2020 are reverse energized to withdraw any scent produced by the false production from reaching the user. In one optional embodiment the withdrawn scent is disposed of by directing the reverse air flow to a charcoal packet, as will be described further hereinto below. Stage 2000, as described above, is then performed. In the event that in stage 2030 the predetermined time has expired, stage 2070, as described above, is performed.

Figure 3A:
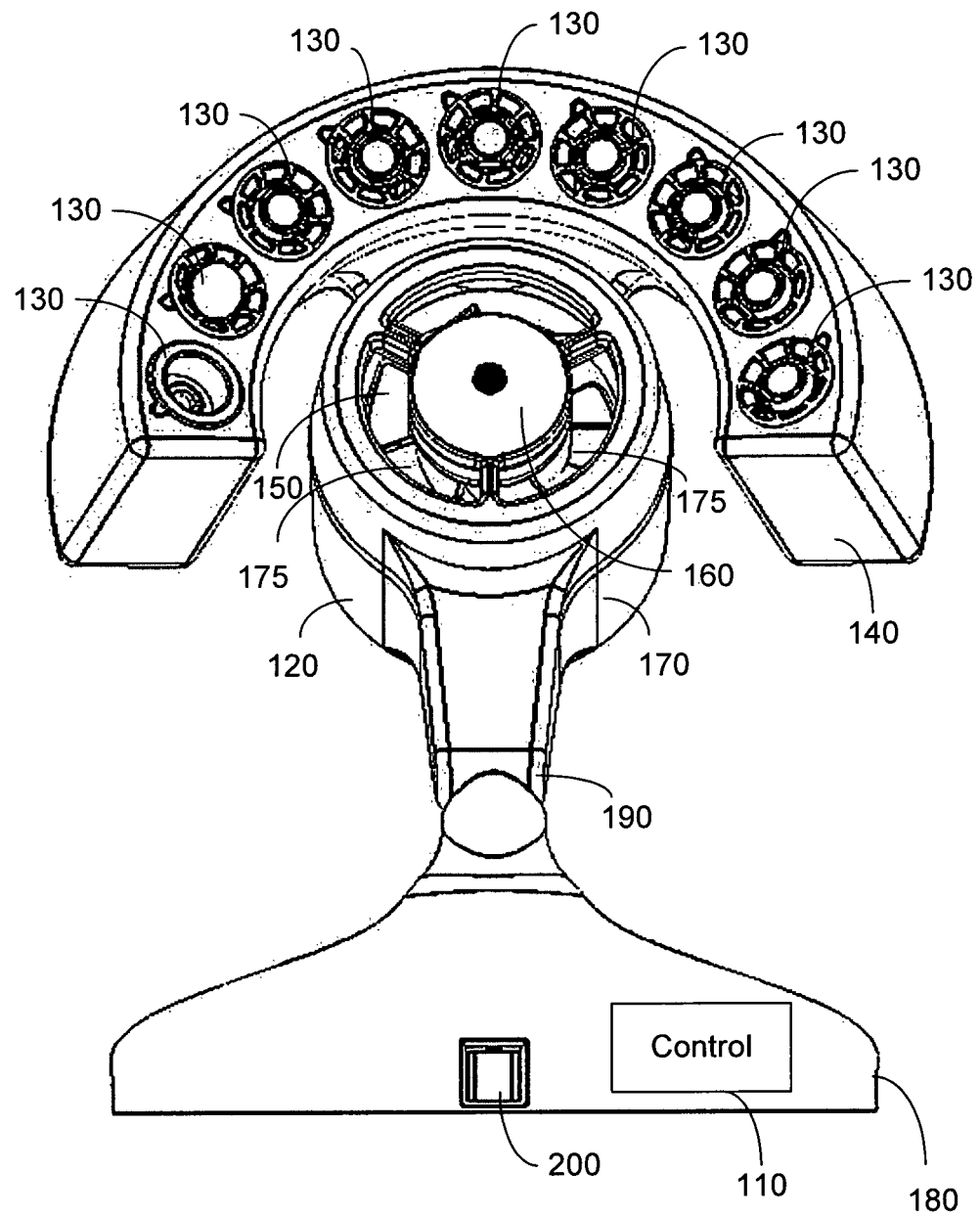
FIGS. 3A-3F illustrate various views of an exemplary embodiment of a scent producing apparatus, the views being described taken together, in accordance with an exemplary embodiment.
Figure 3B:
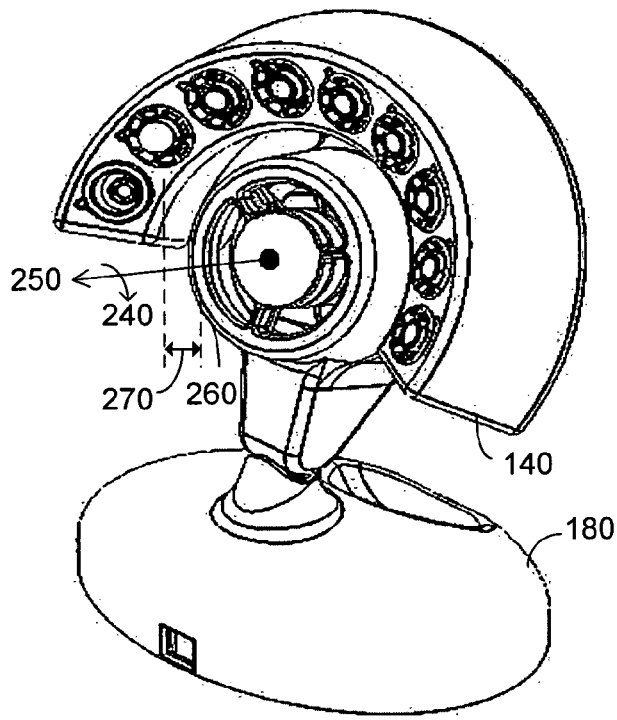
Figure 3C:
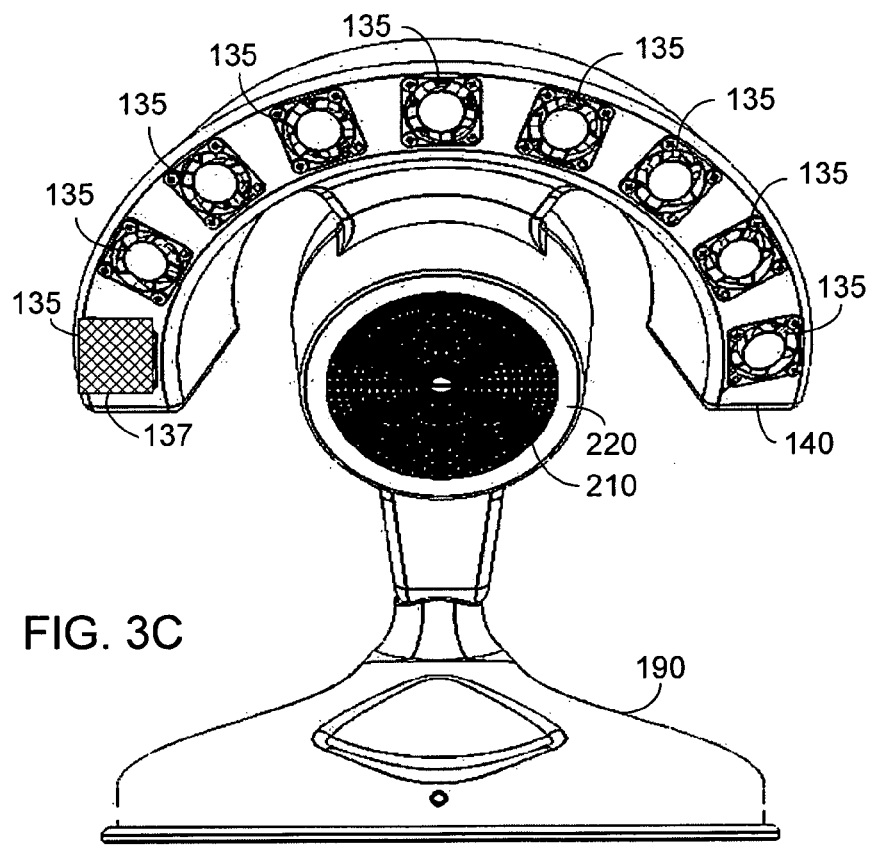
Figure 3D:
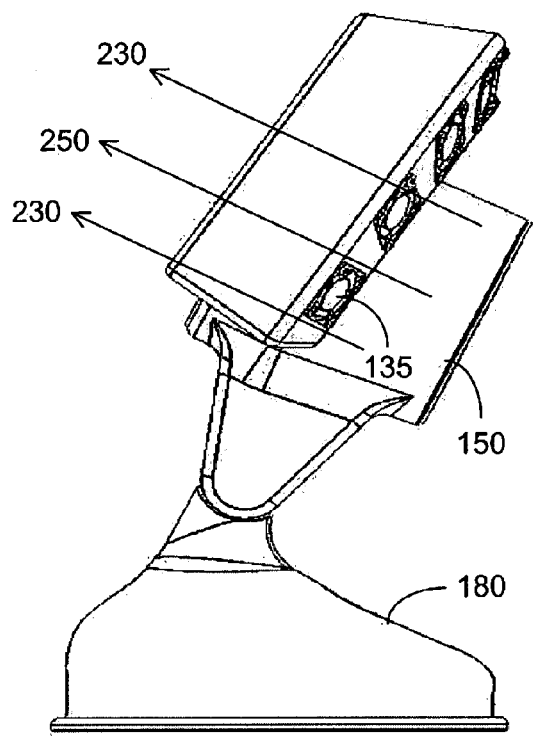
Figure 3E:
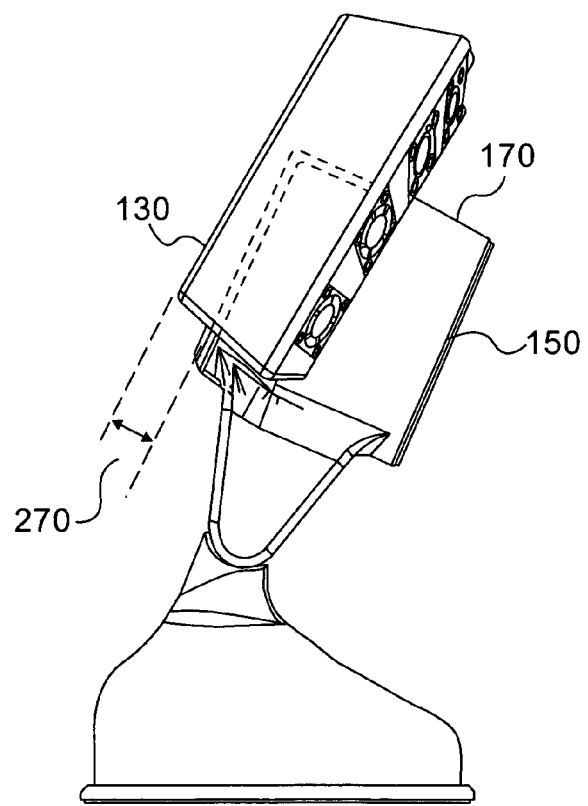
Figure 3F:
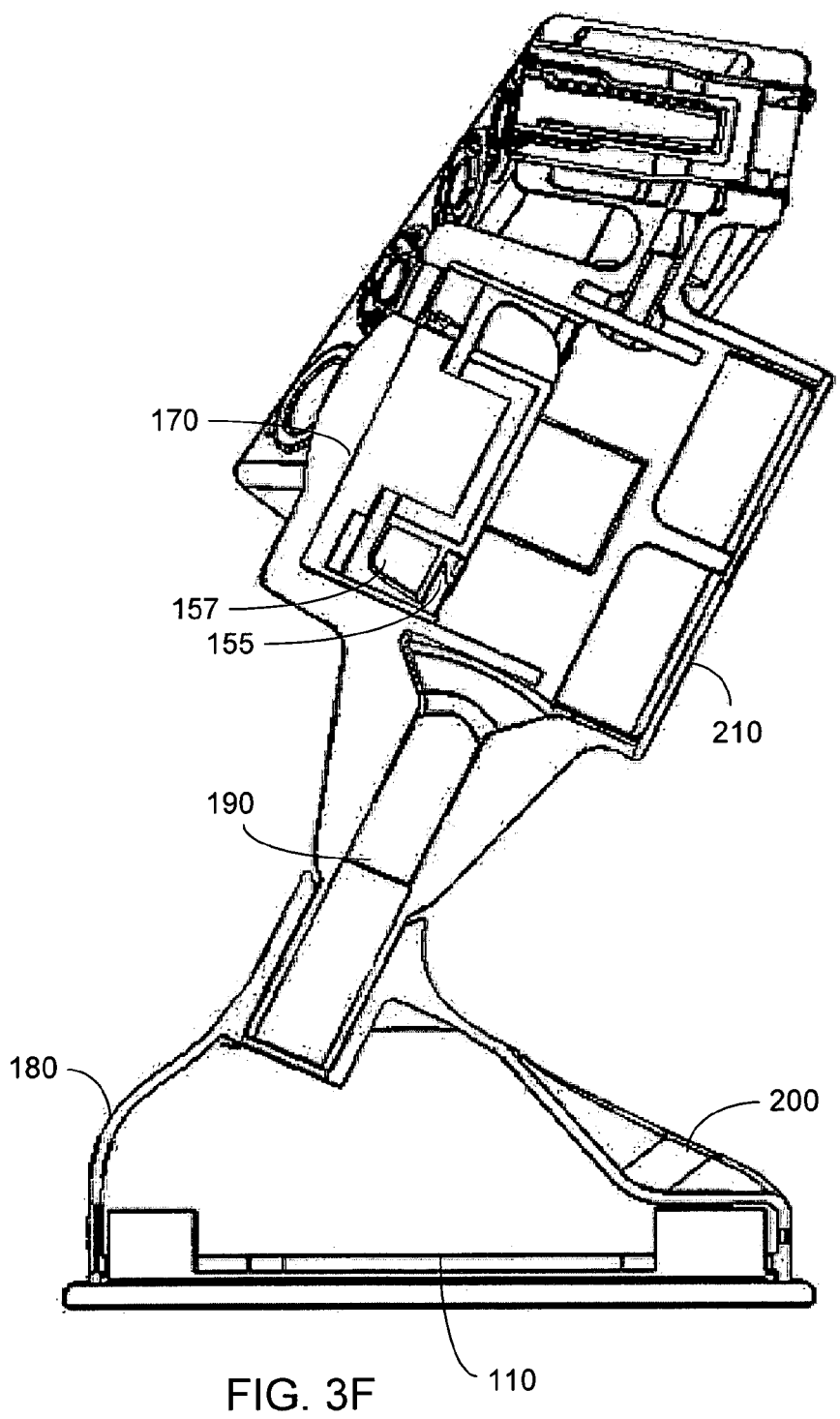

FIGS. 3A-3F illustrate various views of an exemplary embodiment of scent producer 100, the views being described taken together. In particular, FIG. 3A illustrates a frontal view, FIG. 3B illustrates an isometric view, FIG. 30 illustrates a back view, FIG. 3D illustrates a side view, FIG. 3E illustrates a partially cut away side view showing certain spatial relationships and FIG. 3F illustrates a complete cut away side view. Scent producer 100 comprises: control unit 110; directional air mover 120 comprising a fan 150 exhibiting a motor 155 and blades 157, a central member 160 and an air handler 170 forming a plurality of channels 175 and exhibiting a forward end 260; a support member 140 supporting the plurality of electronically controlled scent producing elements 130 each with an associated individual air mover 135 and an optional scent disposer 137, which for clarity is only shown disposed behind a single individual air mover 135 and will be described further in relation to FIG. 4C; a base 180; a telescoping vertical member 190; a connection to computing platform 200; an air filter 210; and a retaining member 220. A direction of air flow 230 is shown, exhibiting an angular velocity 240 with a central axis 250. The distance between forward end 260 of air handler 170 and the output ends of electronically controlled scent producing elements 130 is denoted 270.

Air handler 170 is preferably generally cone shaped, with the apex of the cone facing the direction of air flow shown by arrow 230. Air handler 170 supports fan 150, preferably implemented as an axial fan. Central member 160 is placed distal of fan 150, and is arranged to block air flow in the central inner portion of air handler 170, thus increasing air flow in channels 150. Due to the Venturi effect, the increased air flow through channels 175 further acts to produce a reduced air pressure zone within channels 175, and in the area adjacent to ends of channels 175. Furthermore, the use of axial fan 150, in combination with air handler 170 acts to ensure that the air flow produced by axial fan 150 exits in air flow direction 230 with angular velocity 240, thus exhibiting a vortex like distribution.

Support member 140 is arranged to maintain each electronically controlled scent producing element 130 at a predetermined position in relation to central axis 250 of air flow 230 exiting air handler 170 at front end 260. Preferably, support member 140 is arranged to maintain electronically controlled scent producing elements 130 to be radially arranged about central axis 250. The output ends of each electronically controlled scent producing element 130 are maintained by support member 240 to be distal of front end 260 of air handler 170, and thus any scent molecules output by electronically controlled scent producing element 130 are drawn by the reduced air pressure zone of channels 175. Furthermore, since the output ends of each electronically controlled scent producing element 130 are maintained by support member 240 to be distal of front end 260 of air handler 170, no scent molecules are deposited on air handler 170. Preferably, support member 240 is arranged as approximately a semi-circle, and thus no output scent molecules from any of electronically controlled scent producing elements 130 are drawn by gravity to another portion of support member 240.

Electronically controlled scent producing elements 130 are all shown as being of the same type, with an associated individual air mover 135, however this is not meant to be limiting in any way. A plurality of types of electronically controlled scent elements 130, as will be described further below, may be installed within scent producer 100 without exceeding the scope. Individual air movers 135 are optional, and most of individual air movers 135 are shown without scent disposer 137. Scent disposer 137, shown disposed behind one of the individual air movers 135 is typically constituted of a removable charcoal packet, which in one embodiment is secured within an open frame.

Each electronically controlled scent producing element 130, fan 150 and optional individual air movers 135 are each in communication with control unit 110 and responsive thereto. Optional individual air movers 135 are preferably operative in a forward direction, driving scent output by the associated scent producing element 130 towards central axis 250, and in a reverse direction withdrawing any produced scent from central axis 250, responsive to control unit 110. Fan 150 is preferably operative at a plurality of speeds responsive to control unit 110.

Base 180 supports telescoping vertical member 190, and houses control unit 110, connection to computing platform 200, and power circuits for each of fan 150 and electronically controlled scent producers 130 with associated optional individual air movers, responsive to control unit 110. Telescoping vertical member 190 is preferably hollow and thus allows for passage of electrical connections between control unit 110 and each electronically controlled scent producing elements 130, fan 150 and optional individual air movers 135. Connection to computing platform 200 provides for data communication with computing platform 20 of FIG. 1, and preferably further provides power for operation of scent producer 100. Air filter 210, preferably constituted of an activated charcoal filter, and/or an electrostatic filter, is operative to ensure that residual scents within the area are not driven towards the user by directional air mover 120. Air filter 210 is maintained in place by retaining ring 220.

FIGS. 4A-4C illustrate various exploded views of an exemplary embodiment of an electronically controlled scent producing element 130, denoted electronically controlled scent producing element 130', the views being described taken together. In particular FIG. 4A illustrates an exploded assembly view, FIG. 4B illustrates an assembled isometric front view and FIG. 4C illustrates an isometric back view. Electronic scent producing element 130' comprises: a heating cartridge base 300 exhibiting a flange 310; a heating assembly 320 exhibiting a heating ring 325 and a pair of leads 330; a porous material reservoir 340 exhibiting a flange 350; and a cartridge carrier 360 exhibiting a plurality of stand offs 362 and a plurality of air flow channels 365, with the output side of electronically controlled scent producing element 130' denoted output 370. Cartridge carrier 360 is further shown in FIG. 5B below. FIG. 4C further shows the assembly of electronically controlled scent producing element 130' in cooperation with individual air mover 135 and scent disposer 137. In an exemplary embodiment, porous material reservoir 340 is constituted of compressed melamine, impregnated with a volatile scent fluid. In one non-limiting embodiment, the volatile scent fluid comprises a scent essence available from Frutarom, Inc. of North Bergen, N.J., mixed to produce a volatile liquid with a boiling point above room temperature.

Porous material reservoir 340 is inserted within heating assembly 320, such that heating ring 325 is in contact with flange 350 of porous material reservoir 340. The assembly of porous material reservoir 340 and heating assembly 320 is inserted within heating cartridge base 300, with flange 310 receiving the outer portion of heating ring 325. Heating cartridge base 300 is further inserted within cartridge carrier 360, with flange 350 of porous material reservoir 340 defining output 370. In one embodiment, a top heating element is further supplied crossing over flange 350.

Stand-offs 362 support heating cartridge base 300 within the body of cartridge carrier 360, and are arranged to secure the center longitudinal axis of heating cartridge base 300 aligned with a central longitudinal axis of cartridge carrier 360. Spaces between stand-offs 362 define air flow channels 365 surrounding heating cartridge base 300. Optional individual air mover 135 is attached to the end of cartridge carrier 360 opposing output 370. Optional scent disposer 137 is secured to optional individual air mover 135 further removed from output 370.

In operation, control unit 110 is operative to controllably supply energy to heating ring 325 via leads 330. Heating ring 325 heats a portion of porous material reservoir 340, and particularly flange 350, to bring a portion of the volatile scent fluid impregnated therein to a boiling point. Once the volatile scent fluid has reached the boiling point, the scent begins to be exuded.

In one embodiment, the scent exuded from output 370 is drawn towards air flow 230 by the reduced air pressure caused by the above mentioned Venturi effect of channels 175. Optionally, control unit 110 further energizes individual air mover 135, constituted of an axial fan, to drive an air flow in the forward direction towards output 370 thereby further driving the scent exuded from output 370 toward air flow 230. Optionally, to cease scent production, and particularly in the event of a false prediction as described above in relation to FIG. 2, control unit 110 energizes individual air mover 135 to drive an air flow in the reverse direction away from output 370, thereby withdrawing any scent exuded from output 370 from air flow 320. In such an embodiment, the addition of scent disposer 137 further acts to prevent any non-desired scent exuded from output 370 from reaching the user.

Figure 5A:
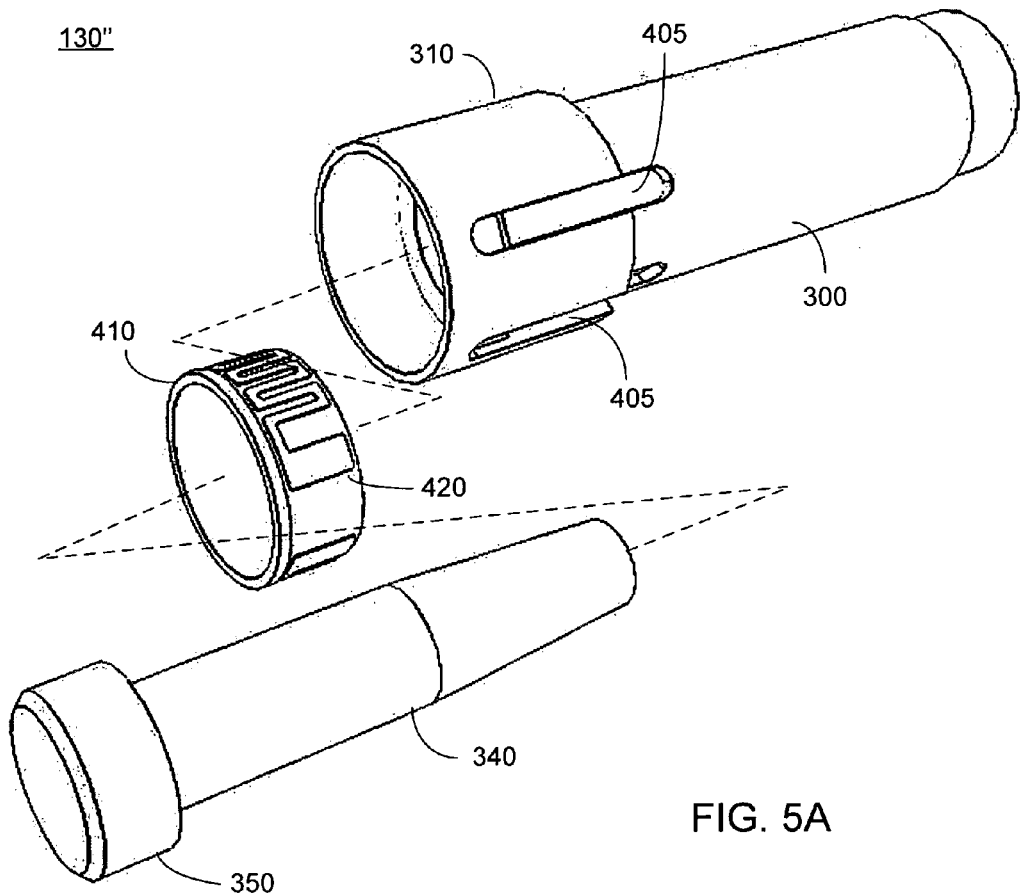
FIGS. 5A-5D illustrate various views of a second exemplary embodiment of an electronically controlled scent producing element comprising a heating element in cooperation with a scent impregnated absorbent material, the views being described taken together, in accordance with an exemplary embodiment.
Figure 5B:
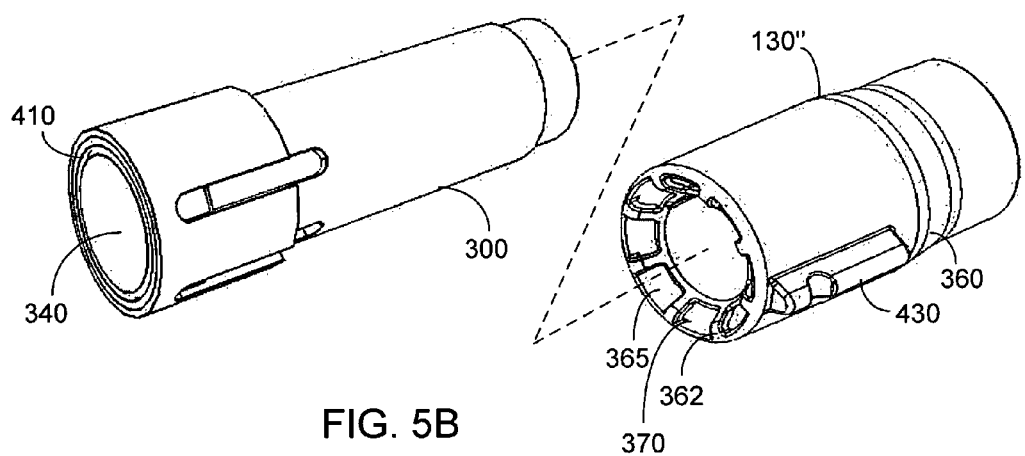
Figure 5C:
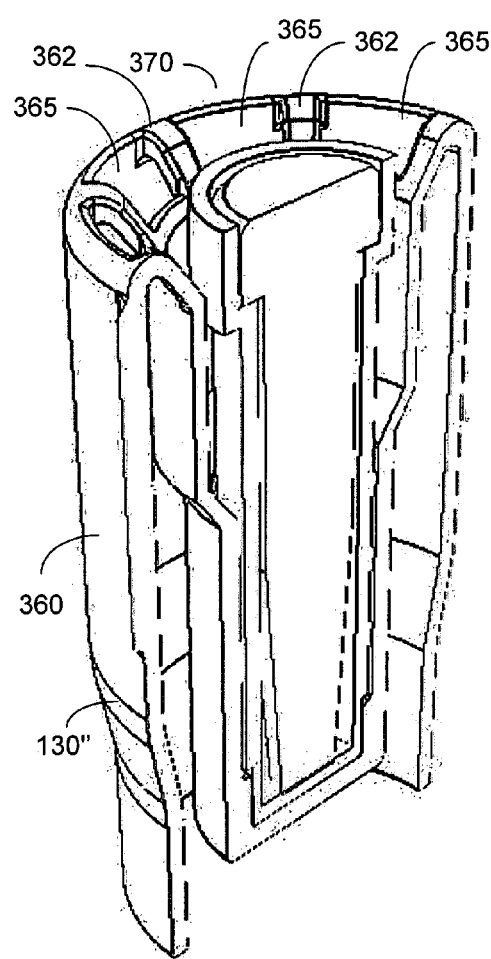
Figure 5D:
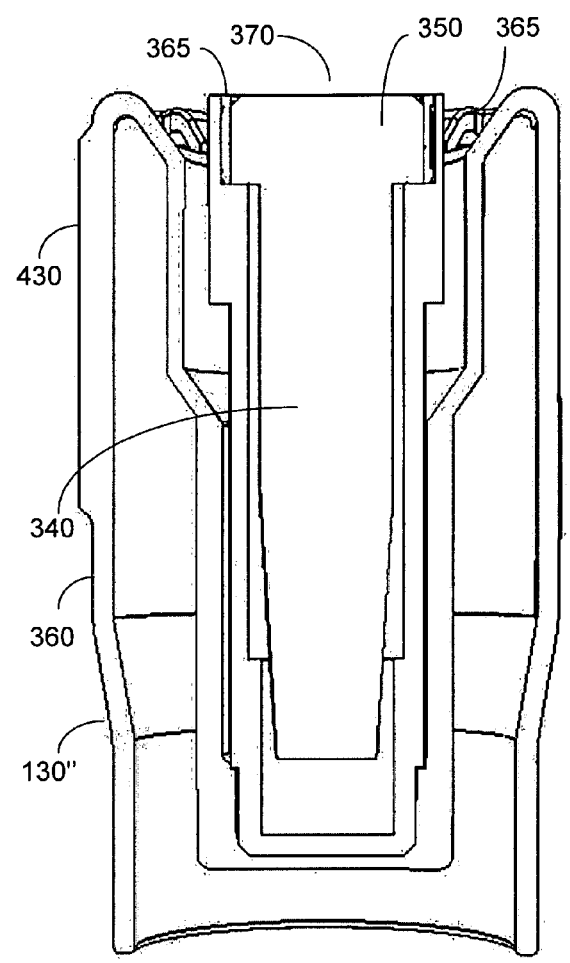

FIGS. 5A-5D illustrate various exploded views of an exemplary embodiment of an electronically controlled scent producing element 130, denoted electronically controlled scent producing element 130", the views being described taken together. In particular FIG. 5A illustrates an exploded assembly view, FIG. 5B illustrates an exploded assembly view of the elements of FIG. 5A inserted into a cartridge carrier 360, FIG. 5C illustrates an isometric cut away view of FIG. 5B and FIG. 5D illustrates a side-on cut away view of FIG. 5B.

Electronic scent producing element 130" comprises: a heating cartridge base 300 exhibiting a flange 310 and lead openings 405; a heating ring 410 comprising a printed heating element 420 disposed on an electrically isolated outer layer thereof; a porous material reservoir 340 exhibiting a flange 350; and a cartridge carrier 360 exhibiting a plurality of stand offs 362, a plurality of air flow channels 365 and a keying element 430, with the output side of electronically controlled scent producing element 130" denoted output 370. Optionally, an individual air mover 135 and scent disposer 137 may be provided as described above in relation to electronically controlled scent producing element 130'. In an exemplary embodiment, porous material reservoir 340 is constituted of compressed melamine, impregnated with a volatile scent fluid. In one non-limiting embodiment, the volatile scent fluid comprises a scent essence available from Frutarom, Inc. of North Bergen, N.J., mixed to produce a volatile liquid with a boiling point above room temperature.

Porous material reservoir 340 is inserted within heating ring 410, such that heating ring 410 is contact with flange 350 of porous material reservoir 340. The assembly of porous material reservoir 340 and heating ring 410 is inserted within heating cartridge base 300, with flange 310 receiving the outer portion of heating ring 325. Heating cartridge base 300 is further inserted within cartridge carrier 360, with flange 350 of porous material reservoir 340 defining output 370.

Stand-offs 362 support heating cartridge base 300 within the body of cartridge carrier 360, and are arranged to secure the center longitudinal axis of heating cartridge base 300 aligned with a central longitudinal axis of cartridge carrier 360. Spaces between stand-offs 362 define air flow channels 365 surrounding heating cartridge base 300. Keying element 430 ensures proper alignment of cartridge carrier 360 within a matching socket of support member 140 and further secures cartridge carrier 360 within the matching socket. Optional individual air mover 135 is attached to the end of cartridge carrier 360 opposing output 370 (not shown). Optional scent disposer 137 is secured to optional individual air mover 135 further removed from output 370 (not shown).

In operation, control unit 110 is operative to controllably supply energy to printed heating element 420 via leads (not shown) extending through lead openings 405. Printed heating element 420 heats heating ring 410 which transfers the thermal energy to a portion of porous material reservoir 340, and particularly flange 350, to bring a portion of the volatile scent fluid impregnated therein to a boiling point. Once the volatile scent fluid has reached the boiling point, the scent begins to be exuded.

In one embodiment, the scent exuded from output 370 is drawn towards air flow 230 by the reduced air pressure caused by the above mentioned Venturi effect of channels 175. Optionally, control unit 110 further energizes individual air mover 135 (not shown), constituted of an axial fan, to drive an air flow in the forward direction towards output 370 thereby further driving the scent exuded from output 370 toward air flow 230. Optionally, to cease scent production, and particularly in the event of a false prediction as described above in relation to FIG. 2, control unit 110 energizes individual air mover 135 to drive an air flow in the reverse direction away from output 370, thereby withdrawing any scent exuded from output 370 from air flow 320. In such an embodiment, the addition of scent disposer 137 (not shown) further acts to prevent any non-desired scent exuded from output 370 from reaching the user.

Figures 6A, 6B, 6C:
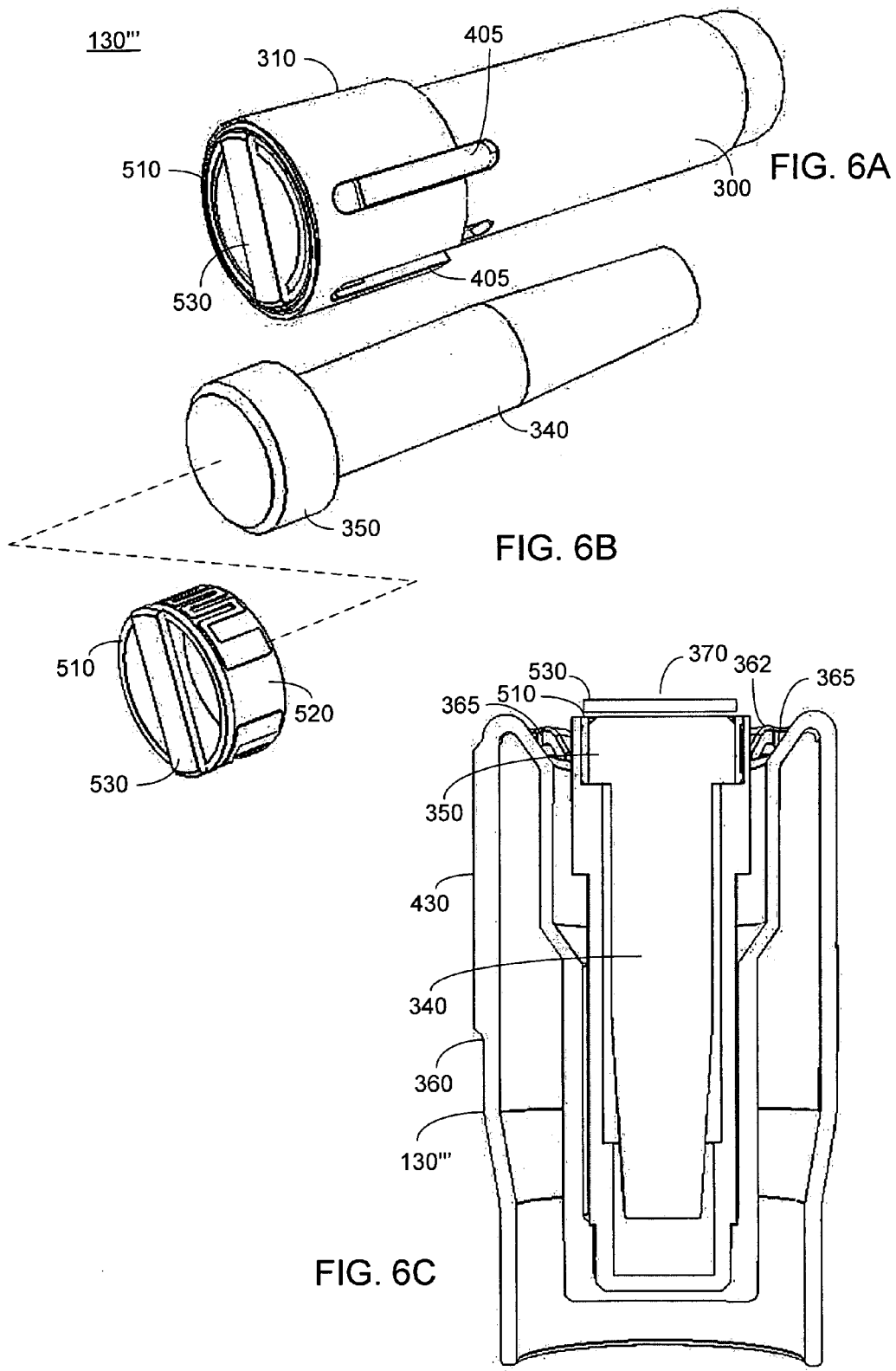
FIGS. 6A-6C illustrate various views of a third exemplary embodiment of an electronically controlled scent producing element comprising a heating element in cooperation with a scent impregnated absorbent material, the views being described taken together, in accordance with an exemplary embodiment.

FIGS. 6A-6C illustrate various exploded views of an exemplary embodiment of an electronically controlled scent producing element 130, denoted electronically controlled scent producing element 130''', the views being described taken together. In particular FIG. 6A illustrates a partially assembled view, FIG. 6B illustrates a partial exploded assembly view and FIG. 6C illustrates a side-on cut away view of assembled scent producing element 130'. Electronic scent producing element 130''' comprises: a heating cartridge base 300 exhibiting a flange 310 and lead openings 405; a heating ring 510 comprising a printed heating element 520 disposed on an electrically isolated outer layer thereof and a heating bar 530 in thermal communication with printed heating element 520 and disposed across a diameter of one end of heating ring 510; a porous material reservoir 340 exhibiting a flange 350; and a cartridge carrier 360 exhibiting a plurality of stand offs 362, a plurality of air flow channels 365 and a keying element 430, with the output side of electronically controlled scent producing element 130''' denoted output 370. Optionally, an individual air mover 135 and scent disposer 137 may be provided as described above in relation to electronically controlled scent producing element 130'. In an exemplary embodiment, porous material reservoir 340 is constituted of compressed melamine, impregnated with a volatile scent fluid. In one non-limiting embodiment, the volatile scent fluid comprises a scent essence available from Frutarom, Inc. of North Bergen, N.J, mixed to produce a volatile liquid with a boiling point above room temperature.

Heating ring 510 is placed over the end of porous material reservoir 340, such that an end of flange 350 of porous material reservoir 340 is in contact with heating bar 350, and flange 350 is further surrounded by heating ring 510. The assembly of porous material reservoir 340 and heating ring 510 is inserted within heating cartridge base 300, with flange 310 receiving the outer portion of heating ring 510. Heating cartridge base 300 is further inserted within cartridge carrier 360, with heating bar 350 consonant with output 370.

Stand-offs 362 support heating cartridge base 300 within the body of cartridge carrier 360, and are arranged to secure the center longitudinal axis of heating cartridge base 300 aligned with a central longitudinal axis of cartridge carrier 360. Spaces between stand-offs 362 define air flow channels 365 surrounding heating cartridge base 300. Keying element 430 ensures proper alignment of cartridge carrier 360 within a matching socket of support member 140 and further secures cartridge carrier 360 within the matching socket. Optional individual air mover 135 is attached to the end of cartridge carrier 360 opposing output 370 (not shown). Optional scent disposer 137 is secured to optional individual air mover 135 further removed from output 370 (not shown).

In operation, control unit 110 is operative to controllably supply energy to printed heating element 520 via leads (not shown) extending through lead openings 405. Printed heating element 520 heats heating ring 510 and heating bar 530 which transfers the thermal energy to a portion of porous material reservoir 340, and particularly flange 350, to bring a portion of the volatile scent fluid impregnated therein to a boiling point. Once the volatile scent fluid has reached the boiling point, the scent begins to be exuded.

In one embodiment, the scent exuded from output 370 is drawn towards air flow 230 by the reduced air pressure caused by the above mentioned Venturi effect of channels 175. Optionally, control unit 110 further energizes individual air mover 135 (not shown), constituted of an axial fan, to drive an air flow in the forward direction towards output 370 thereby further driving the scent exuded from output 370 toward air flow 230. Optionally, to cease scent production, and particularly in the event of a false prediction as described above in relation to FIG. 2, control unit 110 energizes individual air mover 135 to drive an air flow in the reverse direction away from output 370, thereby withdrawing any scent exuded from output 370 from air flow 320. In such an embodiment, the addition of scent disposer 137 (not shown) further acts to prevent any non-desired scent exuded from output 370 from reaching the user.

FIGS. 7A-7B illustrate various exploded views of an exemplary embodiment of an electronically controlled scent producing element 130, denoted electronically controlled scent producing element 130'''', the views being described taken together. In particular FIG. 7A illustrates an isometric cut away view of assembled scent producing element 130' and FIG. 7B illustrates an isometric view of assembled scent producing element 130'. Electronic scent producing element 130'''' comprises: a porous material reservoir 340 exhibiting a flange 350; an intermediate gas permeable element 610, constituted of a top portion 620 and lower portion 630, porous material reservoir 340 contactingly surrounded by intermediate gas permeable element 610; a heating element 640 in thermal communication with top portion 620; and a cartridge carrier 360 exhibiting a plurality of stand offs 362, a plurality of air flow channels 365 and a keying element 430, with the output side of electronically controlled scent producing element 130'''' denoted output 370. Optionally, an individual air mover 135 and scent disposer 137 may be provided as described above in relation to electronically controlled scent producing element 130'. In an exemplary embodiment, porous material reservoir 340 is constituted of compressed melamine, impregnated with a volatile scent fluid. In one non-limiting embodiment, the volatile scent fluid comprises a scent essence available from Frutarom, Inc. of North Bergen, N.J., mixed to produce a volatile liquid with a boiling point above room temperature.

Intermediate gas permeable element 610 is preferably constituted of a material unaffected by the heat of heating element 640 with which it is in contact, and further exhibits thermal transfer properties so as to transfer the thermal energy output by heating element 640 to porous material reservoir 340, and particularly to flange 350 thereof The constituent material of intermediate gas permeable element 610 is selected to be permeable to the scent to be exuded from porous material reservoir 340 when heated. In one non-limiting embodiment intermediate gas permeable element 610 is constituted of a stone or clay based material. Intermediate gas permeable element 610 thus contactingly surrounds porous material reservoir 340 and flange 350, and transfers heat thereto while passing the exuded scent. Bottom element 630 is arranged to receive the lower extension of porous material reservoir 340 and top element 620 is arrange to mate with bottom element 630 and cover flange 350 of porous material reservoir 340, the combination of top element 620 and bottom element 630 preferably completely surrounding and containing porous material reservoir 340. Heating element 640 is in contact with an end of top element 620 opposing the end in contact with flange 350. The assembly of porous material reservoir 340, intermediate gas, permeable element 610, and heating element 640 is inserted within cartridge carrier 360, with heating element 640 consonant with output 370.

Stand-offs 362 support intermediate gas permeable element 610 within the body of cartridge carrier 360, and are arranged to secure the center longitudinal axis of intermediate gas permeable element 610 aligned with a central longitudinal axis of cartridge carrier 360. Spaces between stand-offs 362 define air flow channels 365 surrounding intermediate gas permeable element 610. Keying element 430 ensures proper alignment of cartridge carrier 360 within a matching socket of support member 140 and further secures cartridge carrier 360 within the matching socket. Optional individual air mover 135 is attached to the end of cartridge carrier 360 opposing output 370 (not shown). Optional scent disposer 137 is secured to optional individual air mover 135 further removed from output 370 (not shown).

In operation, control unit 110 is operative to controllably supply energy to heating element 640 via leads (not shown). Heating element 640 heats intermediate gas permeable element 610 which transfers the thermal energy to a portion of porous material reservoir 340, and particularly flange 350, to bring a portion of the volatile scent fluid impregnated therein to a boiling point. Once the volatile scent fluid has reached the boiling point, the scent begins to be exuded and passes through intermediate gas permeable element 610 to exit at output 370.

In one embodiment, the scent exuded from output 370 is drawn towards air flow 230 by the reduced air pressure caused by the above mentioned Venturi effect of channels 175. Optionally, control unit 110 further energizes individual air mover 135 (not shown), constituted of an axial fan, to drive an air flow in the forward direction towards output 370 thereby further driving the scent exuded from output 370 toward air flow 230. Optionally, to cease scent production, and particularly in the event of a false prediction as described above in relation to FIG. 2, control unit 110 energizes individual air mover 135 to drive an air flow in the reverse direction away from output 370, thereby withdrawing any scent exuded from output 370 from air flow 320. In such an embodiment, the addition of scent disposer 137 (not shown) further acts to prevent any non-desired scent exuded from output 370 from reaching the user.

Figure 8F:
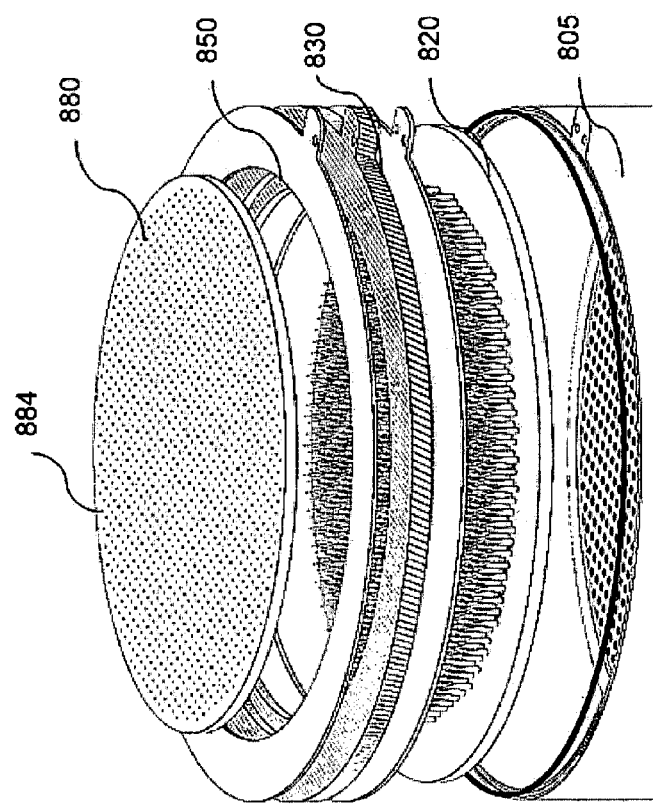
Figure 8E:
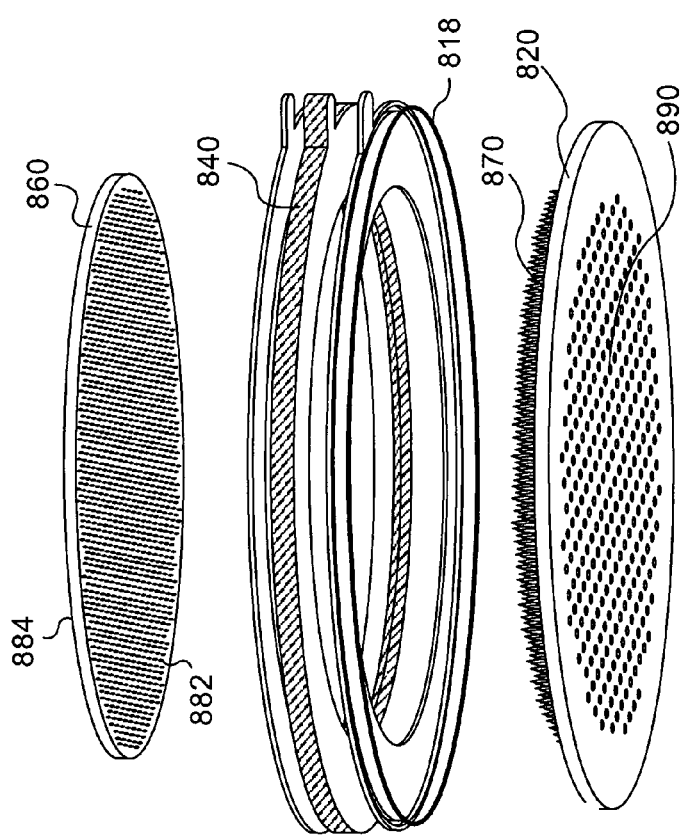
Figure 8H:
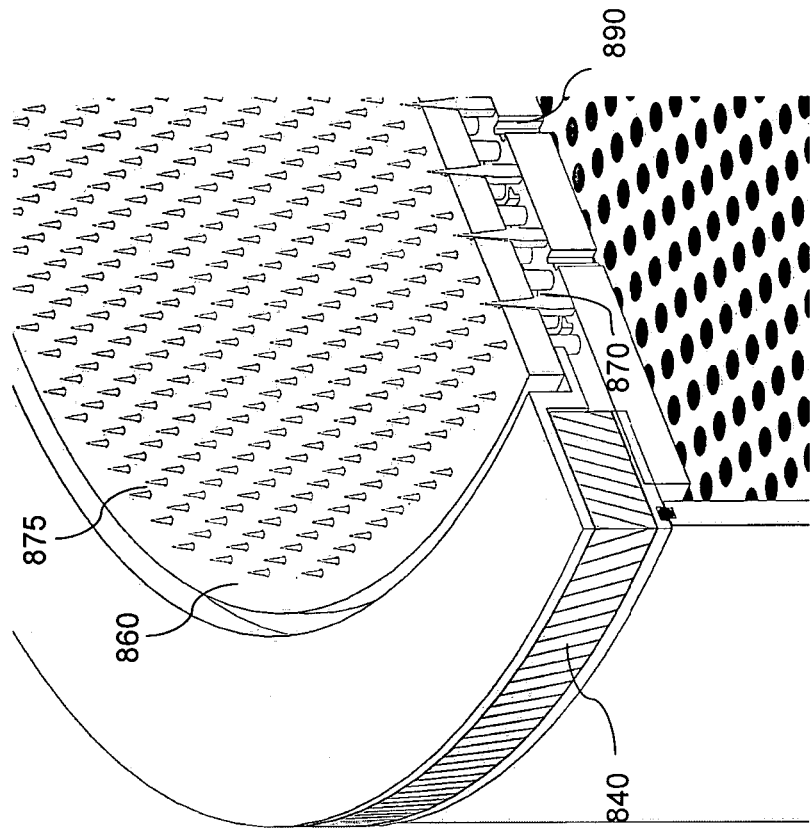
Figure 8G:
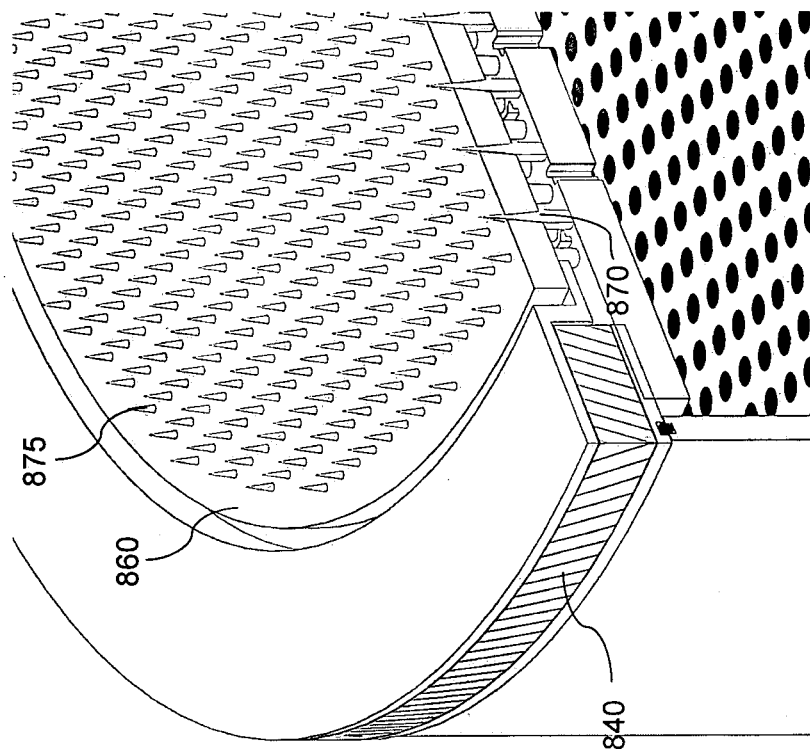
Figure 8J:
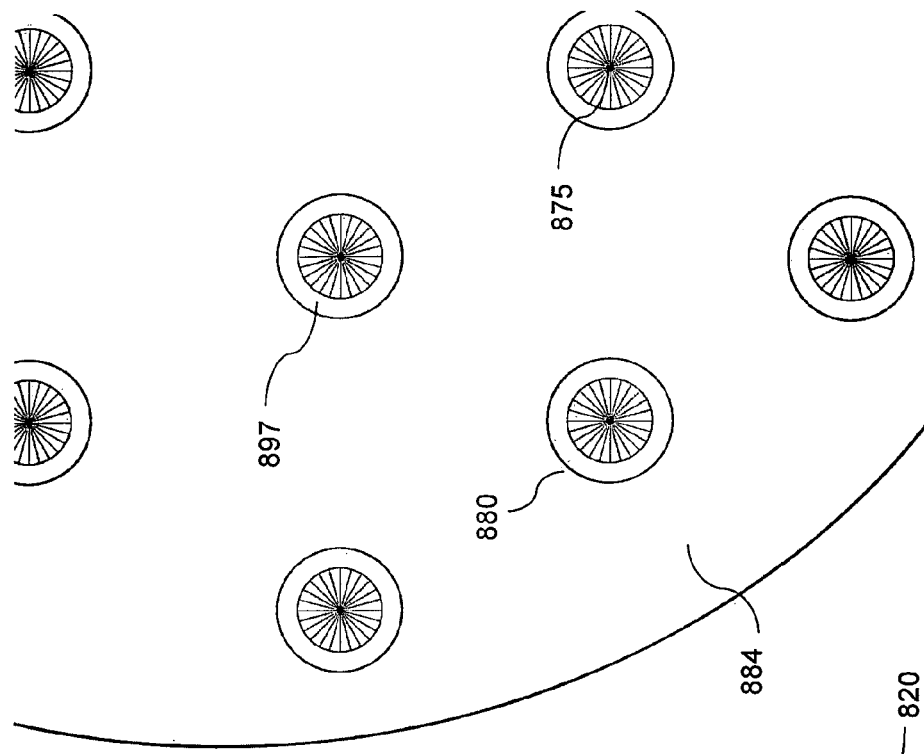
Figure 8I:
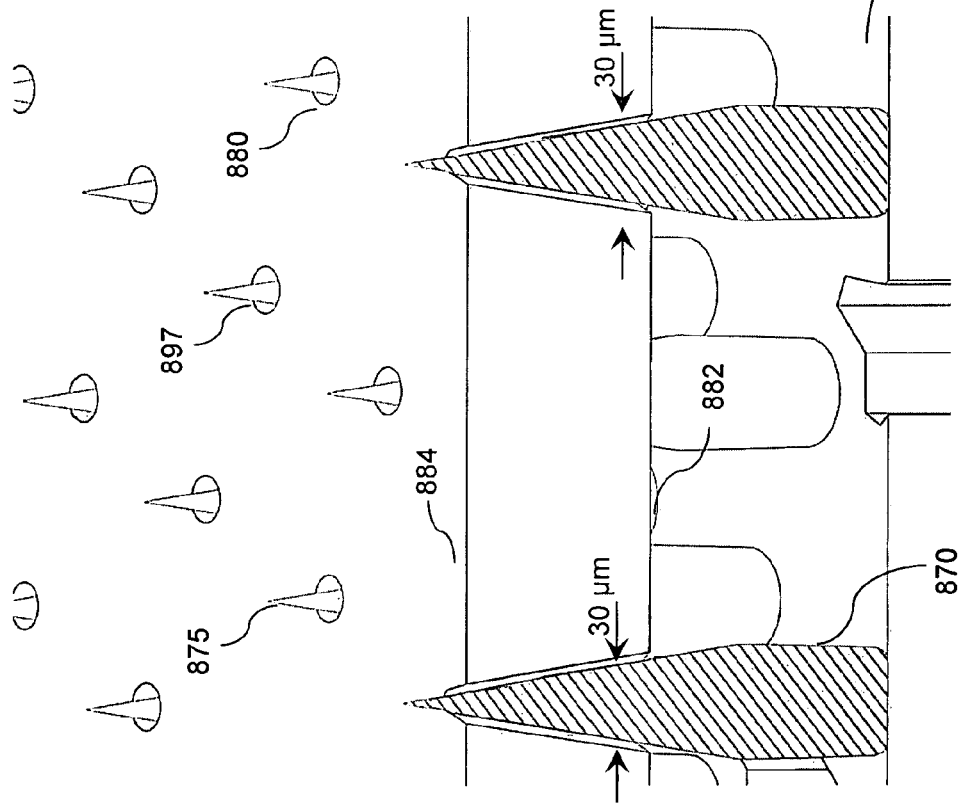

FIGS. 8A-8J illustrate various exploded views of an exemplary embodiment of an electronically controlled scent producing element 800, the views being described taken together. Electronically controlled scent producing element 800 may be used in place of electronically controlled scent producing element 130, or independently, without exceeding the scope. Electronically controlled scent producing element 800 may be further be used to nebulize, or atomize, any liquid, such as a medicament, without exceeding the scope. In particular, FIG. 8A illustrates an isometric view of electronically controlled scent producing element 800; FIG. 8B illustrates a more detailed view of a top portion of electronically controlled scent producing element 800 of FIG. 8A; FIG. 8C illustrates an isometric cut away view of electronically controlled scent producing element 800; FIG. 8D illustrates a more detailed view of the top portion of FIG. 8B; FIG. 8E illustrates a first exploded view of electronically controlled scent producing element 800; FIG. 8F illustrates a second exploded view of electronically controlled scent producing element 800; FIG. 8G illustrates a first position for certain portions of electronically controlled scent producing element 800; FIG. 8H illustrates a second position for certain portions of electronically controlled scent producing element 800; FIG. 8I illustrates a highly detailed view of the perforations and plugs of electronically controlled scent producing element 800; and FIG. 8J illustrates the resultant shape of scent producing liquid droplets, in accordance with an exemplary embodiment.

Electronically controlled scent producing element 800 comprises: a container 805; a lower reservoir 810; a unidirectional flow membrane 815; an upper reservoir 816; a sealing ring 818; a plug base 820; a first electrode 830; a piezoelectric element 840; a second electrode 850; and a plate 860. Plate 860 exhibits a plurality of perforations 880 extending from first face 882 to second face 884. Plug base 820 exhibits a plurality of pass through channels 890, and a plurality of micro-plugs 870 extending longitudinally from a base portion attached to plug base 820 to a tip end 875, with each plug arranged to mate with a respective one of perforations 880. Preferably, a portion of each plug 870, and particularly the portion extending through perforations 880 are conically shaped with an apex extending away from plug base 820. Perforations 880 are preferably similarly conically shaped, such that when plug base 820 is brought to its closest position in relation to first face 882, micro-plugs 870 are seated flush against the inner walls of the respective perforation 880. Preferably, perforations 880 exhibit a diameter of about 30 microns at first face 882, matching the diameter of micro-plugs 870 when completely seated therein. The space created towards second face 884 when each micro-plug 870 is separated from the respective perforation 880 is denoted space 895, and a ring shaped droplet 897 of volatile scent liquid is formed by the shape of plug 870 in proximity of second face 884.

Sealing ring 818 is provided of a compliant material so as to form a seal against liquid, in particular a volatile scent liquid. Unidirectional flow membrane 815, in cooperation with container 805, forms lower reservoir 810. Unidirectional flow membrane 815, in cooperation with plug base 820, forms upper reservoir 816. In particular, unidirectional flow membrane 815 defines the top of lower reservoir 810 and the bottom of upper reservoir 816. The top of upper reservoir 816 is defined by one end of plug base 820 in particular the side not exhibiting micro-plugs 870. First electrode 830 is placed at one side of piezoelectric element 840, in electrical contact therewith, and in physical contact with plug base 820, in particular the side of plug base 820 exhibiting micro-plugs 870. Piezoelectric element 840 is preferably a ring shaped element, and second electrode 850 is placed on the second side of piezoelectric element 840, in electrical contact therewith. Plate 860 is placed in physical contact with second electrode 850, and in one embodiment is secured thereto with an adhesive to prevent the escape of plate 860. Face 882 of plate 860 is juxtaposed with plug base 820 such that each micro-plug 870 extends into a matching perforation 880. The combination of micro-plugs 870 and perforations 880 forms an ultrasonic micro-plug unit.

In a first mode of operation, as illustrated in FIGS. 8G and 8H, a low frequency electric power is applied to piezoelectric element 840, and in response piezoelectric element 840 expands, separating plug base 820 from plate 860 shown in FIG. 8G as being in closest proximity, to a separated position as illustrated in FIG. 8H-8J. After expansion, an additional high frequency electrical power is further supplied, superimposed on the low frequency electrical power, vibrating piezoelectric element 840. In an exemplary embodiment the high frequency electrical power exhibits a frequency range of 150-200 kHz, however this is not meant to be limiting in any way. The preferred conical shape of micro-plugs 870 function to focus the acoustical energy supplied by piezoelectric element 840 towards tip ends 875, thereby atomizing any volatile scent liquid in contact with micro-plugs 870 and within perforations 880 so as to be scented distal of second face 884. Advantageously, the conical shape of micro-plugs 870 forms ring shaped droplet 897, which requires a reduced amount of energy to atomize, or nebulize, when compared to a standard droplet of volatile scent liquid. Advantageously, the amount of separation between plug base 820 and plate 860 may be varied responsive to the viscosity of the liquid being atomized or nebulized thus varying the dimensions of the ring shaped aperture produced by micro-plugs 870 in cooperation with perforations 880, and thus a single ultrasonic micro-plug unit may be utilized for liquids having a wide range of viscosity without being blocked.

In a second mode of operation, electrical power is disconnected from piezoelectric element 840, and in response piezoelectric element 840 contracts bringing plug base 820 into closer proximity with plate 860 until micro-plugs 870 are seated flush within perforations 880, i.e. a closed position, thus sealing the volatile scent liquid from second face 884, and preventing any further scent from being experienced distal of second face 884. The particular conical shape mentioned above results in a complete seal, which is preferred for use with a volatile scent liquid, however this is not meant to be limiting in any way. In another embodiment a complete seal is not required in the second mode, but only that the plurality of micro-plugs travel sufficiently through perforations 880 to ensure that no residual liquid remains within perforations 880 to prevent occlusion.

In a third mode of operation, while micro-plugs 870 are seated flush within perforations 880, a medium to high frequency electrical power, in one non-limiting embodiment being from 40 kHz to 400 kHz, is supplied to piezoelectric element 840, thus vibrating the combination of plate 860 and micro-plugs 870. Any residual volatile scent on tip ends 875 and second face 884 is promptly atomized, or nebulized, and removed thus completely ceasing scent production.

Figure 9B:
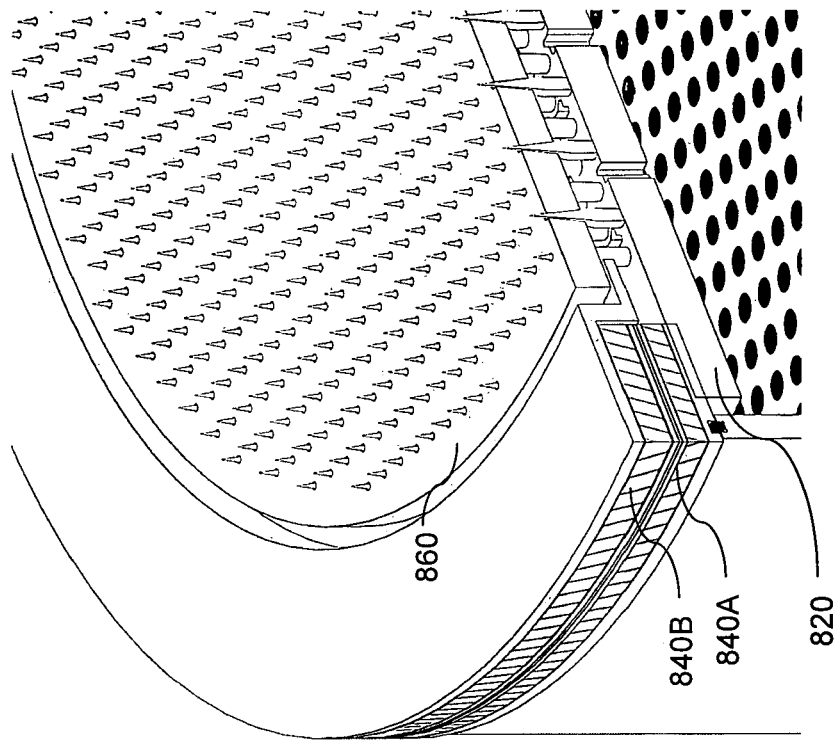
FIGS. 9A and 9B illustrate a first alternative embodiment for the scent producing element of FIG. 8A, in which a separate translation mechanism and vibrator are supplied in a stacked manner, in accordance with an exemplary embodiment.
Figure 9A:
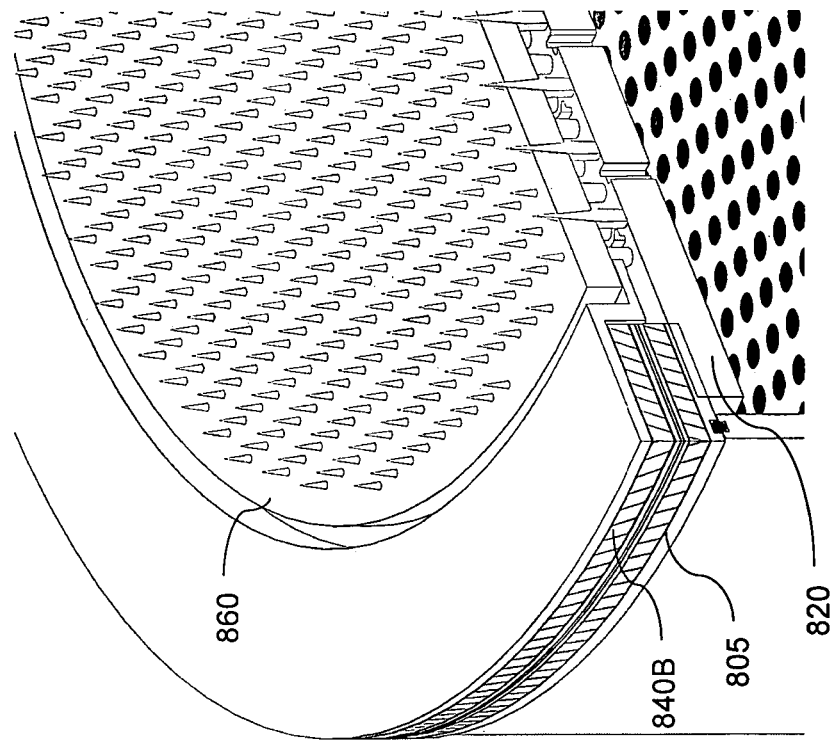

FIGS. 9A and 9B illustrate a first alternative embodiment for electronically controlled scent producing element 800, in which a plurality of elements 840 are supplied in a stacked manner, a first element being a translation mechanism 840A and a second element being a vibrator 840B. In particular, a pair of piezoelectric elements is provided, each provided with a pair of electrodes, and physically stacked. Translation mechanism 840A translates plug base 820 in relation to plate 860 between a first closed position, as shown in FIG. 9A, wherein plug base 820 is proximate plate 860 to a second open position as shown in FIG. 9B, wherein plug base 820 is removed from plate 860. Vibrator 840B operates as described above to vibrate plug base 820 and plate 860 thereby controllably producing a scent. The combination of micro-plugs 870 and perforations 880 forms an ultrasonic micro plug unit.

Figure 10A:
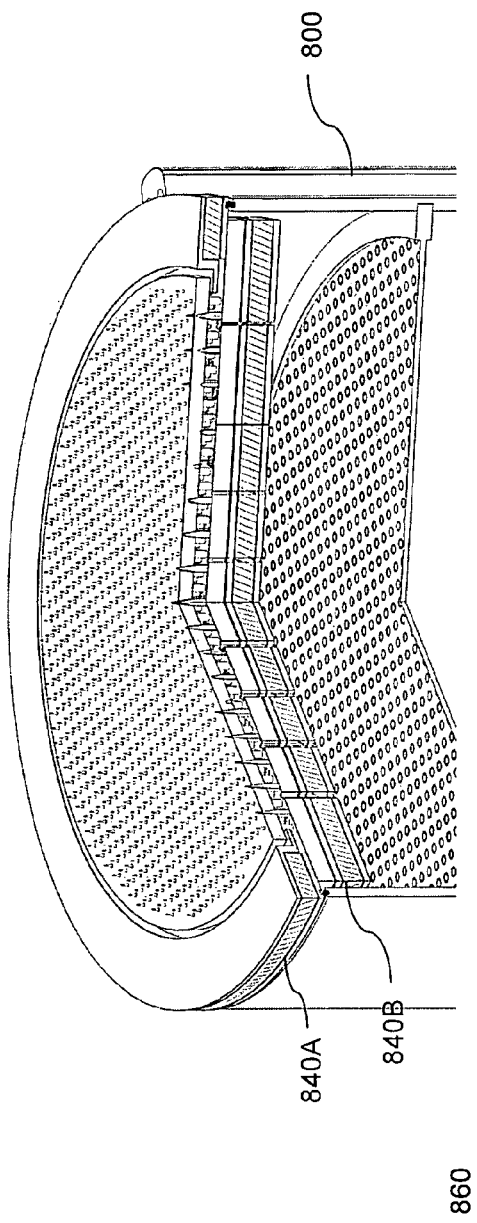
FIGS. 10A-10C illustrate a second alternative embodiment for the scent producing element of FIG. 8A, in which a separate translation mechanism and vibrator are supplied in disparate locations, in accordance with an exemplary embodiment.
Figure 10C:
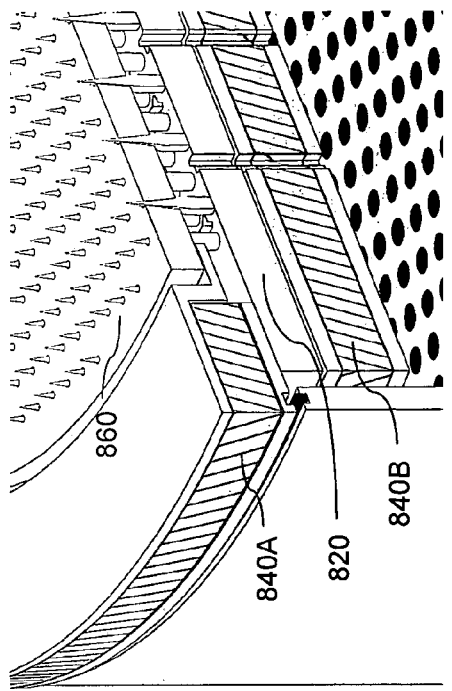
Figure 10B:
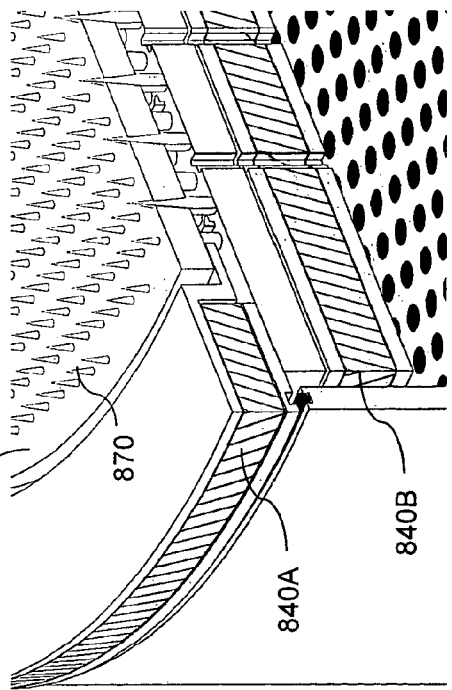

FIGS. 10A-10C illustrate a second alternative embodiment for electronically controlled scent producing element 800, in which a plurality of elements 840 are supplied, a first element being a translation mechanism 840A and a second element being a vibrator 840B, in which plate 860 is fixed, and vibration energy is supplied only to plug base 820. FIG. 10A illustrates a cut away view of the second alternative embodiment, FIG. 10B illustrates the second alternative embodiment in a closed position wherein plug base 820 is proximate plate 860, and FIG. 10C illustrates the second alternative embodiment in an open position wherein plug base 820 is removed from plate 860.

In particular, plurality of elements 840 is a pair of piezoelectric elements, each provided with a pair of electrodes. Translation mechanism 840A is in communication with plate 860 and is seated against a rim of the container. Vibrator 840B is in communication with plug base 820 and mechanically isolated from plate 860. The combination of micro-plugs 870 and perforations 880 forms an ultrasonic micro plug unit.

In a first mode of operation a low frequency electric power is applied to translation mechanism 840A, and in response translation mechanism 840A expands, separating plate 860 from base plate 820, particular by separating plate 860 from the rim of container 805. A high frequency electrical power is further supplied to vibrator 840B thus vibrating micro-plugs 870. Micro-plugs 870, exhibiting the preferred conical shape, act as a micro-acoustic lens, breaking the volatile second liquid received via pass through channels 890 into micro-drops, thus atomizing any volatile scent liquid in contact with micro-plugs 870 and within perforations 880 so as to be scented distal of second face 884. Advantageously, as described above in relation to FIGS. 8I-8J, the shape of micro-plugs 870 are arranged to form ring shaped droplet 897, which requires a reduced amount of energy to atomize, or nebulize, when compared to a standard droplet of volatile scent liquid. In an exemplary embodiment the high frequency electrical power exhibits a frequency range of 150-200 kHz, however this is not meant to be limiting in any way. Advantageously, the amount of separation between plug base 820 and plate 860 may be varied responsive to the viscosity of the liquid being atomized or nebulized thus varying the dimensions of the ring shaped aperture produced by micro-plugs 870 in cooperation with perforations 880, and thus a single ultrasonic micro-plug unit may be utilized for liquids having a wide range of viscosity without being blocked.

In a second mode of operation, electrical power is disconnected from translation mechanism 840A, and in response translation mechanism 840A contracts bringing plate 860 into closer proximity with plug base 820 until micro-plugs 870 are seated flush within perforations 880, i.e. a closed position, thus sealing the volatile scent liquid from second face 884, and preventing any further scent from being experienced distal of second face 884. The particular conical shape mentioned above results in a complete seal, which is preferred for use with a volatile scent liquid, however this is not meant to be limiting in any way. In another embodiment a complete seal is not required in the second mode, but only that the plurality of micro-plugs travel sufficiently through perforations 880 to ensure that no residual liquid remains within perforations 880 to prevent occlusion.

FIGS. 11A-11C illustrate a third alternative embodiment for electronically controlled scent producing element 800, in which a plurality of elements 840 are supplied, a first element being a translation mechanism 840A and a second element being a vibrator 840B, in which vibration energy is supplied only to plate 820 via a member 910 passing through unidirectional flow membrane 815. FIG. 11A illustrates a cut away view of the third alternative embodiment, FIG. 11B illustrates the third alternative embodiment in a closed position wherein plug base 820 is proximate plate 860, and FIG. 11C illustrates the third alternative embodiment in an open position wherein the plate 860 is moved from the plug base 820. A sealing ring 818 is further supplied providing a seal between plate 860 and a flange 915 connected to the walls of electronically controlled scent producing element 800.

In particular, plurality of elements 840, particularly translation mechanism 840A and vibrator 840B, is a pair of piezoelectric elements, each provided with a pair of electrodes. Translation mechanism 840A and vibrator 840B are each in contact with plate 860 via member 910. Vibrator 840B is mechanically isolated from plug base 820.

In a first mode of operation a low frequency electric power is applied to translation mechanism 840A, and in response translation mechanism 840A expands, separating plate 860 from base plate 820 of micro-plugs 870, to a scent producing position. A high frequency electrical power is further supplied to vibrator 840B thus vibrating plate 860 and atomizing liquid in contact with first face 882. In an exemplary embodiment the high frequency electrical power exhibits a frequency range of 150-200 kHz, however this is not meant to be limiting in any way. Advantageously, the amount of separation between plug base 820 and plate 860 may be varied responsive to the viscosity of the liquid being atomized or nebulized thus varying the dimensions of the ring shaped aperture produced by micro-plugs 870 in cooperation with perforations 880, and thus a single ultrasonic micro-plug unit may be utilized for liquids having a wide range of viscosity without being blocked.

In a second mode of operation, electrical power is disconnected from, or supplied inverted to, translation mechanism 840A, and in response translation mechanism 840A contracts, bringing plate 860 into closer proximity with plug base 820 until micro-plugs 870 are seated flush within perforations 880, i.e. a closed position, thus sealing the volatile scent liquid from second face 884, and preventing any further scent from being experienced distal of second face 884. The particular conical shape mentioned above results in a complete seal, which is preferred for use with a volatile scent liquid, however this is not meant to be limiting in any way. In another embodiment a complete seal is not required in the second mode, but only that the plurality of micro-plugs travel sufficiently through perforations 880 to ensure that no residual liquid remains within perforations 880 to prevent occlusion.

In a third mode of operation, while micro-plugs 870 are seated flush within perforations 880, a medium to high frequency electrical power, in one non-limiting embodiment being from 40 kHz to 400 kHz, is supplied to piezoelectric element 840, thus vibrating the combination of plate 860 and micro-plugs 870. Any residual volatile scent on tip ends 875 and second face 884 is promptly atomized, or nebulized, and removed thus completely ceasing scent production.

FIG. 12 illustrates a high level schematic diagram of a driving circuit useable with electronically controlled scent producing element 800 of FIGS. 8A-11C, comprising a pulse generator 950, a driver 960, a first piezoelectric element 840A and a second piezoelectric element 840B, an electrical characteristic sense circuit 970 and control circuit 980. Pulse generator 950 preferably comprises a low frequency functionality 952, a high frequency functionality 954 and an ultrasonic cleaning functionality 956. Control circuit 980 is in communication with each of pulse generator 950, driver 960 and electrical characteristic sense circuit 970. The output of pulse generator 950, which may comprise a plurality of outputs as illustrated, is connected via driver 960, to a first contact of each of first piezoelectric element 840A and second piezoelectric element 840B, respectively. The second contact of each of first piezoelectric element 840A and second piezoelectric element 840B, are respectively to electrical characteristic sense circuit 970, which may comprise a sense resistor and a comparator arranged to compare the voltage drop across the sense resistor with a value supplied by control circuit 980. In the event that a single piezoelectric element 840 is provided, one of pulse generator 950 and driver 960 are arranged to provide a combined signal to piezoelectric element 840.

In operation, and as described above, control circuit 980 operates low frequency functionality 952 to generate a low frequency electrical power, which is driven towards piezoelectric element 840 by driver 960, and is operative, for example, to separate plate 860 from base plate 820. High frequency functionality 954 is arranged to vibrate one or more of plate 860 and base plate 820. In particular modes, responsive to control circuit 980, ultrasonic cleaning functionality 956 is operative in the absence of both low frequency electrical power from low frequency functionality 952 and high frequency electrical power from high frequency functionality 954 to perform ultrasonic cleaning by providing vibrating energy to base plate 820 and plate 860 while seated flush.

Control circuit 980 is further operative to monitor at least one electrical characteristic of piezoelectric element 840 in combination with the vibrated elements, via electrical characteristic sense circuit 970. In a first mode of operation, the natural resonant frequency of piezoelectric element 840 in combination with the vibrated elements is found by sweeping, or stepping through, a range of frequencies. The natural frequency exhibits the lowest resistance to electrical current flow, and thus by monitoring the amount of current flow through piezoelectric element 840 responsive to high frequency functionality 954, the natural resonant frequency of piezoelectric element 840 in combination with the vibrated elements is found. In the event that the natural resonant frequency does not match an integer function of frequencies supplied by high frequency functionality 954, in one embodiment the frequency is toggled between one just above and just below the natural resonant frequency to achieve an average of the natural resonant frequency.

The natural resonant frequency is a function of liquid volume in communication with piezoelectric element 840, the vibrated elements, temperature and age of piezoelectric element 840. Thus, in the event that the found natural resonant frequency is indicative, due to the parameters being outside of a predetermined range, that an insufficient amount of volatile scent liquid is in communication with piezoelectric element 840, control circuit 980 is operative to assert a low liquid alarm signal.

Figure 12:
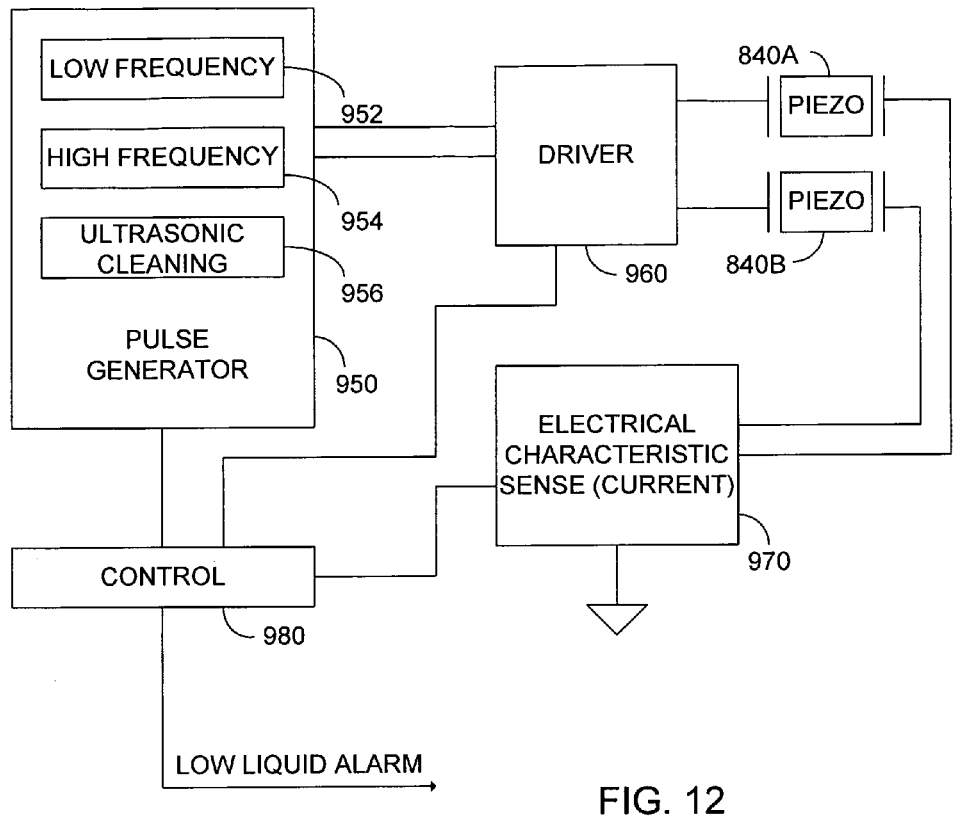
FIG. 12 illustrates a high level schematic diagram of a driving circuit useable with scent producing element 800 of any of FIGS. 8A-11C.
Figure 13:
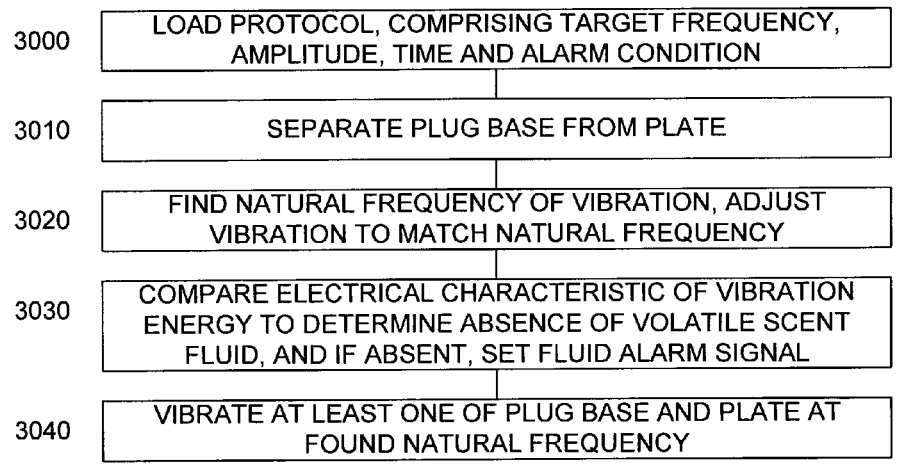
FIG. 13 illustrates a high level flow chart of the operation of control circuit of FIG. 12, in accordance with an exemplary embodiment.

FIG. 13 illustrates a high level flow chart of the operation of control circuit 980 of FIG. 12, in accordance with an exemplary embodiment. In stage 3000, a protocol is loaded by control circuit 980, preferably comprising a target frequency for low frequency functionality 952, a target frequency for high frequency functionality 954, a driving amplitude for driver 960, a length of time for operation, an operation mode and a low fluid alarm condition. In one non-limiting example, a scent producing protocol comprises a low frequency target value of 50 Hz, a low frequency amplitude of 20V, a high frequency target value of 159 kHz, a high frequency amplitude of 30V, a length of time of 2 seconds, and a pulsed mode of operation. In one non-limiting example, a cleaning protocol comprises a low frequency target value of 0 Hz, a low frequency amplitude of 0V, a high frequency target value of 50 kHz, a high frequency amplitude of 25V, a length of time of 6 seconds, and a continuous mode of operation. As described above the amplitude of driver 960 may be set for electrical power responsive to low frequency functionality 952, thus the amount of separation between plug base 820 and plate 860 may be varied responsive to the viscosity of the liquid being atomized or nebulized, and thus a single ultrasonic micro-plug unit may be utilized for liquids having a wide range of viscosity without being blocked.

In stage 3010, control circuit 980 is operative to separate plate 860 from plug base 820 by operating a translation mechanism. In an exemplary embodiment, the translation mechanism is a piezoelectric element 840A with a signal responsive to low frequency functionality 952. The amplitude of the low frequency signal is controlled by driver 960 responsive to the loaded protocol of stage 3000.

In stage 3020, the natural frequency of vibration is found and the frequency of vibration being driven by pulse generator 950, and in particular by high frequency functionality 954 is modified to match the natural frequency of vibration, by sweeping or steeping above and below the loaded high frequency target frequency of stage 3000. In the event that the natural resonant frequency does not match an integer function of frequencies supplied by high frequency functionality 954, in one embodiment the frequency is toggled between one just above and just below the natural resonant frequency to achieve an average of the natural resonant frequency.

In stage 3030, the electrical characteristic at the found natural frequency of vibration is compared with a predetermined range loaded as part of the protocol of stage 3000. In the event that the found natural frequency of vibration, or the electrical characteristic at the found natural frequency of vibration, is not with the predetermined range, but is instead indicative of a lack of volatile scent liquid an out of fluid alarm signal is asserted.

In stage 3040, at least one of plug base 820 and plate 860 is vibrated at the found natural frequency of stage 3020, in accordance with the operation mode and length of time of operation, loaded as part of the protocol of stage 3000.

It is appreciated that certain features of the invention, which are, for clarity, described in the context of separate embodiments, may also be provided in combination in a single embodiment. Conversely, various features of the invention which are, for brevity, described in the context of a single embodiment, may also be provided separately or in any suitable sub-combination.

Unless otherwise defined, all technical and scientific terms used herein have the same meanings as are commonly understood by one of ordinary skill in the art to which this invention belongs. Although methods similar or equivalent to those described herein can be used in the practice or testing of the present invention, suitable methods are described herein.

All publications, patent applications, patents, and other references mentioned herein are incorporated by reference in their entirety. In case of conflict, the patent specification, including definitions, will prevail. In addition, the materials, methods, and examples are illustrative only and not intended to be limiting.

It will be appreciated by persons skilled in the art that the present invention is not limited to what has been particularly shown and described hereinabove. Rather the scope of the present invention is defined by the appended claims and includes both combinations and sub-combinations of the various features described hereinabove as well as variations and modifications thereof, which would occur to persons skilled in the art upon reading the foregoing description.

I claim:

1. An apparatus for producing a scent, the apparatus comprising:
a directional air mover arranged to produce an air flow exhibiting an angular velocity in relation to a central linear axis of said air flow;
a plurality of electronically controlled scent producing elements arranged about said produced air flow, each of said plurality of electronically controlled scent producing elements distal of said directional air mover such that scent from any of said plurality of electronically controlled scent producing elements are not deposited on any surface of said directional air mover; and
a control unit in communication with each of said directional air mover and said plurality of electronically controlled scent producing elements,
wherein each of said electronically controlled scent producing elements further comprises an electronically controlled air mover responsive to said control unit, said control unit arranged to:
energize the electronically controlled air mover, of one of the plurality of electronically controlled scent producing elements, in a first direction to drive the scent output of the one of the plurality of electronically controlled scent producing elements towards said air flow; and energize the electronically controlled air mover, of the one of the plurality of electronically controlled scent producing elements, in a second direction, opposing said first direction, to withdraw the scent output of the one of the plurality of electronically controlled scent producing elements from said air flow, each of said electronically controlled scent producing elements further comprising a scent disposer in communication with said withdrawn scent output.

2. The apparatus according to claim 1, wherein said plurality of electronically controlled scent producing elements are arranged radially about the central linear axis of said air flow.

3. The apparatus according to claim 1, wherein said directional air mover comprises:
   a fan; and
   an air handler in communication with said fan, said air handler arranged to produce a reduced pressure zone at the output of each of said plurality of electronically controlled scent producing elements, thereby drawing the scent output from each of said electronically controlled scent producing elements into said turbulent air flow.

4. The apparatus according to claim 3, wherein said air handler further comprises at least one central member disposed within said turbulent air flow arranged to increase the air flow rate around the central member.

5. The apparatus according to claim 3, wherein said directional air mover further comprises at least one element arranged to impart an angular velocity to said air flow, said at least one element arranged on an inner surface of said air handler.

6. The apparatus according to claim 1, wherein said scent disposer comprises charcoal.

7. The apparatus according to claim 1, wherein said control unit is arranged to actuate more than one of the plurality of electronically controlled scent producing elements and energize the respective electronically controlled air movers of the actuated electronically controlled scent producing elements in the first direction to produce a single combined scent.

8. The apparatus according to claim 1, wherein each of said electronically controlled scent producing elements comprises:
   a scent impregnated absorbent material; and
   a heating element responsive to said control unit and in thermal contact with said scent impregnated absorbent material,
   wherein said scent impregnated absorbent material generates a particular scent when heated by said heating element to a predetermined temperature.

9. The apparatus according to claim 8, further comprising an intermediate gas permeable element, said scent impregnated absorbent material at least partially contactingly surrounded by said intermediate gas permeable element, said heating element arranged to heat said intermediate gas permeable element.

* * * * *